US010098955B2

(12) United States Patent
Shorr et al.

(10) Patent No.: US 10,098,955 B2
(45) Date of Patent: *Oct. 16, 2018

(54) PHARMACEUTICAL FORMULATIONS CONTAINING LIPOIC ACID DERIVATIVES

(71) Applicant: Rafael Pharmaceuticals, Inc., Cranbury, NJ (US)

(72) Inventors: Robert G. L. Shorr, Edison, NJ (US); Robert J. Rodriguez, West Windsor, NJ (US); Rajinder Bhasin, Coram, NY (US)

(73) Assignee: Rafael Pharmaceuticals, Inc., Cranbury, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/662,612

(22) Filed: Jul. 28, 2017

(65) Prior Publication Data

US 2018/0104341 A1    Apr. 19, 2018

Related U.S. Application Data

(63) Continuation of application No. 14/857,192, filed on Sep. 17, 2015, now Pat. No. 9,839,691, which is a continuation of application No. 13/569,654, filed on Aug. 8, 2012, which is a continuation of application No. 12/604,763, filed on Oct. 23, 2009, now Pat. No. 8,263,653, which is a continuation-in-part of application No. 12/105,100, filed on Apr. 17, 2008.

(60) Provisional application No. 60/912,605, filed on Apr. 18, 2007.

(51) Int. Cl.
| | |
|---|---|
| *A61K 31/20* | (2006.01) |
| *A61K 47/18* | (2017.01) |
| *A61K 31/19* | (2006.01) |
| *A61K 31/381* | (2006.01) |
| *A61K 45/06* | (2006.01) |
| *A61K 47/22* | (2006.01) |
| *A61K 47/36* | (2006.01) |
| *A61K 47/54* | (2017.01) |

(52) U.S. Cl.
CPC .............. *A61K 47/18* (2013.01); *A61K 31/19* (2013.01); *A61K 31/20* (2013.01); *A61K 31/381* (2013.01); *A61K 45/06* (2013.01); *A61K 47/183* (2013.01); *A61K 47/22* (2013.01); *A61K 47/36* (2013.01); *A61K 47/541* (2017.08); *Y02A 50/409* (2018.01); *Y02A 50/475* (2018.01); *Y02A 50/479* (2018.01)

(58) Field of Classification Search
CPC ....... A61K 31/20; A61K 47/18; A61K 47/541
See application file for complete search history.

(56) References Cited

U.S. PATENT DOCUMENTS

| | | | |
|---|---|---|---|
| 2,805,251 A | 9/1957 | Marshall et al. |
| 2,809,978 A | 10/1957 | Holly et al. |
| 2,852,531 A | 9/1958 | Hoffman et al. |
| 2,875,238 A | 2/1959 | Holly et al. |
| 2,875,239 A | 2/1959 | Holly et al. |
| 2,975,198 A | 3/1961 | Reed |
| 2,980,716 A | 4/1961 | Reed |
| 2,985,685 A | 5/1961 | Thomas et al. |
| 3,002,011 A | 9/1961 | Holly et al. |
| 3,345,368 A | 10/1967 | Lewis et al. |
| 3,453,312 A | 7/1969 | Sprague |
| 3,881,017 A | 4/1975 | Vlattas |
| 3,970,670 A | 7/1976 | Vlattas |
| 4,041,047 A | 8/1977 | Vlattas |
| 4,077,979 A | 3/1978 | Vlattas |
| 4,077,980 A | 3/1978 | Vlattas |
| 4,705,867 A | 11/1987 | Giray et al. |
| 4,800,044 A | 1/1989 | Giray et al. |
| 4,966,732 A | 10/1990 | Giray et al. |
| 5,344,941 A | 9/1994 | Samour et al. |
| 5,463,093 A | 10/1995 | Garnett |
| 5,508,275 A | 4/1996 | Weithmann et al. |
| 5,569,670 A | 10/1996 | Weischer et al. |
| 5,679,697 A | 10/1997 | Garnett |
| 5,750,141 A | 5/1998 | Roberts et al. |
| 6,117,902 A | 9/2000 | Quash et al. |
| 6,331,559 B1 | 12/2001 | Bingham et al. |
| 6,951,887 B2 | 10/2005 | Bingham et al. |
| 7,220,428 B2 | 5/2007 | Shorr et al. |
| 7,387,790 B2 | 6/2008 | Shorr et al. |
| 7,521,066 B2 | 4/2009 | Shorr et al. |
| RE43,295 E | 4/2012 | Shorr et al. |
| 8,263,653 B2 | 9/2012 | Shorr et al. |
| 8,691,873 B2 | 4/2014 | Shorr et al. |
| 8,785,475 B2 | 7/2014 | Bingham et al. |
| 9,150,509 B2 | 10/2015 | Bingham et al. |
| 9,320,726 B2 | 4/2016 | Shorr et al. |

(Continued)

FOREIGN PATENT DOCUMENTS

| | | |
|---|---|---|
| GB | 758897 A | 10/1956 |
| JP | 2007/077066 A | 3/2007 |

(Continued)

OTHER PUBLICATIONS

U.S. Appl. No. 15/875,655 Pharmaceutical Formulations Containing Lipoic Acid Derivatives, filed Jan. 19, 2018.

A.F. Michaelis and T. Higuchi, in J. Pharm. Sci. (1969) vol. 58, pp. 201-204.

Adams (1955) "Thioctic-$S^{35}{}_2$ Acid: Synthesis and Radiation Decomposition" JACS 77:5357-5359.

Automated CellTiter-Glo® Luminescent Cell Viability Assay Protocol, Promega, Part # EP014, (2009).

(Continued)

*Primary Examiner* — Timothy P Thomas

(74) *Attorney, Agent, or Firm* — Dechert LLP

(57) ABSTRACT

Pharmaceutical formulations containing lipoic acid derivatives and ion pairs thereof are described. The pharmaceutical formulations are useful in the treatment of medical disorders, such as cancer.

22 Claims, 17 Drawing Sheets

(56) References Cited

U.S. PATENT DOCUMENTS

| | | |
|---|---|---|
| 9,839,691 B2 | 12/2017 | Shorr et al. |
| 9,872,845 B2 | 1/2018 | Shorr et al. |
| 2005/0048008 A1 | 3/2005 | Gupta |
| 2008/0262034 A1 | 10/2008 | Bingham et al. |
| 2008/0262077 A1 | 10/2008 | Shorr et al. |
| 2009/0036356 A1 | 2/2009 | Patell et al. |
| 2010/0190858 A1 | 7/2010 | Shorr et al. |
| 2012/0178812 A1 | 7/2012 | Shorr et al. |
| 2013/0150445 A1 | 6/2013 | Shorr et al. |
| 2015/0011633 A1 | 1/2015 | Shorr et al. |
| 2015/0322103 A1 | 11/2015 | Shorr et al. |
| 2016/0220678 A1 | 8/2016 | Shorr et al. |
| 2017/0056355 A1 | 3/2017 | Shorr et al. |

FOREIGN PATENT DOCUMENTS

| | | |
|---|---|---|
| JP | 4728481 B2 | 7/2011 |
| WO | WO-2000/024734 A1 | 5/2000 |
| WO | WO-2009/110859 A1 | 9/2009 |

OTHER PUBLICATIONS

Bastin et al. "Salt Selection and Optimisation Procedures for Pharmaceutical New Chemical Entities," Organic Process Research & Development, 2000, vol. 4, pp. 427-435.

Benson "Transdermal Drug Delivery: Penetration Enhancement Techniques," Current Drug Delivery, vol. 2, No. 1, pp. 23-33 (2005).

Berge S. et al. (1977) "Pharmaceutical Salts," Journal of Pharmaceutical Sciences, 66(1): 1-19.

Crévisy et al. (1998) "A New Iron-Mediated Strategy for the Synthesis of α-Lipoic Acid and Analogues" Eur. J. Org. Chem. pp. 1949-1954.

Daigo et al. (1962) "Synthesis of Some N-Lipoyl Amino Acids and Peptides" J. Am. Chem. Soc. 84(4):662-665.

English Translation of Nakano et al. in Yakugaku Zasshi (1956), 76, 943-7.

Handbook of Pharmaceutical Salts: Properties, Selection and Use, IUPAC, Wiley-VCH, P.H. Stahl ed., p. 342.

International Preliminary Report on Patentability for International Application No. PCT/US2008/060650 dated Dec. 7, 2009, (6 pages).

International Search Report and Written Opinion for International Application No. PCT/US2010/053728 dated Mar. 24, 2011 (9 pages).

International Search Report for International Application No. PCT/US2008/060650 dated Jul. 18, 2008 (1 page).

Johar D. et al. (2004) "Inflammatory response, reactive oxygen species, programmed (necrotic-like and apoptotic) cell death and cancer" Roczniki Akademni Medycznej w Bialymstoku, vol. 49, Annales Academiae Medicae Bialostocensis, pp. 31-39.

Kieler et al. (1967) "The Effect of Structural Analogues of α-lipoic Acid on the Growth and Metabolism of L-Fibroblasts and Ehrlich Cells" Archivum Immunologiae et Therapiae Experimentalis, vol. 15, pp. 106-108.

Nakano (1956) "Studies on α-Lipoic Acid and its Related Compounds. IV. On Acetylation of Ethyl DL-Dihydro-α-lipoate" Yakugaku Zasshi, 76(10):1207-1209. (with English abstract).

Nakano et al. (1955) "Studies on α-Lipoic Acid and its Related Compounds. I. Synthesis of DL-α-Lipoic Acid" Yakugaku Zasshi, 75(10):1296-1298. (with English abstract).

National Toxicology Program (NTP) (1999). Toxicology and Carcinogenesis Studies of Triethanolamine (CAS No. 102-71-6) in F344/N Rats and B6C3F1 Mice (Dermal Studies), NTP TR 449, NIH Publication No. 00-3365.

Pan et al. (1998) "D,L-S-Methyllipoic Acid Methyl Ester, a Kinetically Viable Model for S-protonated Lipoic Acid as the Oxidizing Agent in Reductive Acyl Transfers Catalyzed by the 2-Oxoacid Dehydrogenase Multienzyme Complexes" Biochemistry 37(5):1357-1364.

Patani et al. (1996) "Bioisosterism: A Rational Approach in Drug Design" Chem. Rev., 96:3147-3176.

Rastetter et al. (1981) "α-Keto Acid Dehydrogenases: A Chemical Model" J. Org. Chem. 46(9):1882-1887.

Reed et al. (1955) "Synthesis of DL-α-Lipoic Acid" J. Amer. Chem. Soc. 77:416-419.

Schoberl et al. (1958) Justus Liebigs Ann. Chem. 614:66-83.

Search Report from European Patent Application No. 08780538.8 dated Feb. 24, 2012 (5 pages).

Serajuddin (2007) "Salt formation to improve drug solubility" ScienceDirect, Advanced Drug Delivery Reviews, vol. 59, pp. 603-616.

Shih et al. (1974) "Properties of Lipoic Acid Analogs" J. Heterocycl. Chem. 11:119-123.

Soper et al. (1954) "Syntheses of DL-α-Lipoic Acid" J. Am. Chem. Soc. 76:4109-12.

Stott et al.(2004) "Evaluation of the Potential of Triethanolamine to Alter Hepatic Choline Levels in Female B6C3F1 Mice" Toxicological Sciences, vol. 79, pp. 242-247.

Supplementary European Search Report and Search Opinion dated May 19, 2010 in European Patent Application No. 08780538 (7 pages).

Surya Kanta De, "Yttrium Triflate As an Efficient and Useful Catalyst for Chemoselective Protection of Carbonyl Compounds," Tetrahedron Letters, vol. 45, pp. 2339-2341 (2004).

T. Higuchi and K. Kato, J. Pharm. Sci. (1966) vol. 55, pp. 1080-1084.

T. Higuchi et al., Anal. Chem. (1967) vol. 39, pp. 974-979.

Thomas et al. (1955) "Synthesis and Properties of High Specific Activity DL-α-Lipoic Acid-$S_2^{35}$" J. Am. Chem. Soc. 77(20):5446-5448.

Thomas et al. (1956) "Synthesis of DL-1,2-Dithiolane-3-Caproic Acid and DL-1,2-Dithiolane-3-Butyric Acid, Homologs of α-Lipoic Acid" J. Am. Chem. Soc. 78(23):6151-6153.

Watabe et al. (2007) "ATP depletion does not account for apoptosis induced by inhibition of mitochondrial electron transport chain in human dopaminergic cells" Neuropharmacology 52(2):536-541.

Zong et al. (2006) "Necrotic death as a cell fate" Genes & Development, vol. 20, pp. 1-15.

Thiesen et al., "Physico-chemical stability of docetaxel premix solution and docetaxel infusion solutions in PVC bags and polyolefine containers" (1999), Pharm, World Sci., 21(3), pp. 137-141.

Kintzel et al. "Practical guidelines for preparing and administering amphotericin B", 1992, Am. J. Hosp. Pharm., 49(5): 1156-64, Pub Med abstract, PMID: 1595747.

https://clinicaltrials.gov/ct2/results?term=cpi-613&Search=Search, accessed Apr. 8, 2015.

https://clinicaltrials.gov/ct2/show/NCT01832857?term=cpi-613+colon&rank=2, accessed Apr. 8, 2015.

https://clinicaltrials.gov/ct2/show/NCT01766219?term-cpi-613+liver &rank=1, accessed Apr. 8, 2015.

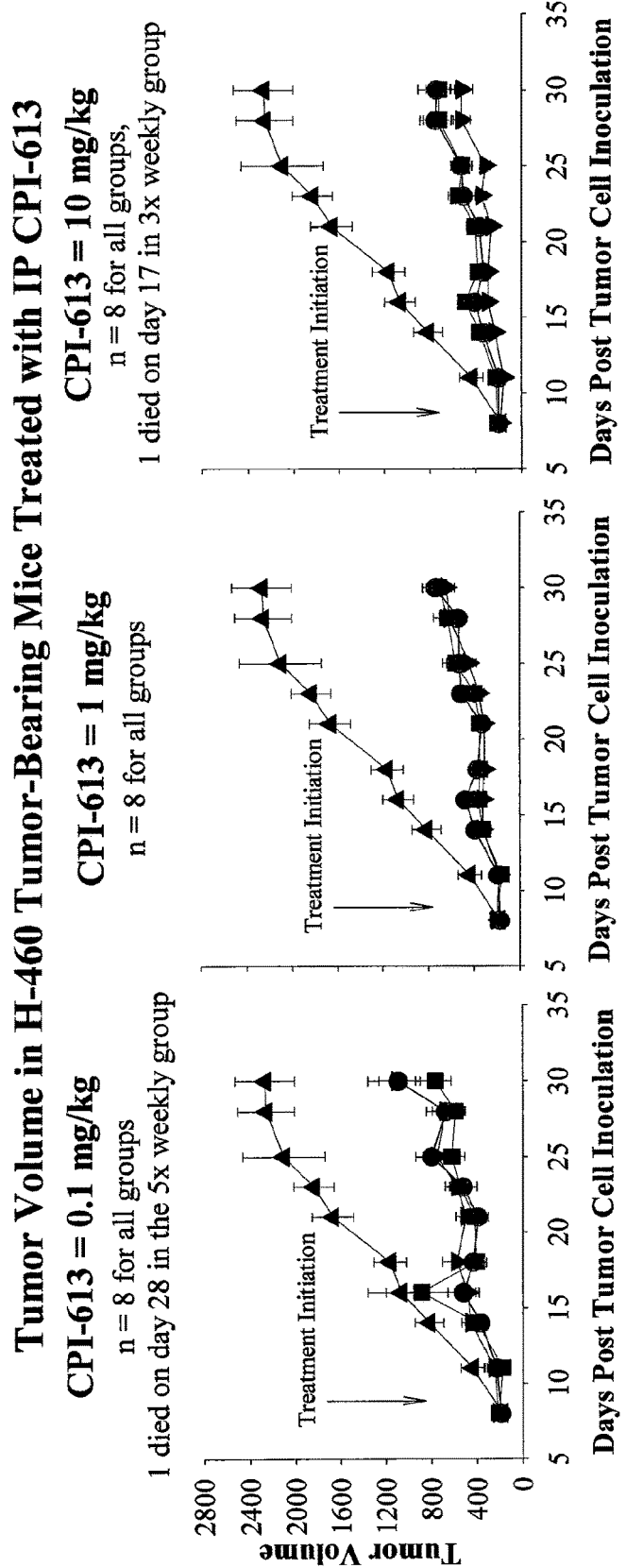

PHARMACEUTICAL FORMULATIONS CONTAINING LIPOIC ACID DERIVATIVES

RELATED APPLICATIONS

This application is a continuation of U.S. patent application Ser. No. 14/857,192, filed Sep. 17, 2015, which is a continuation of U.S. patent application Ser. No. 13/569,654, filed Aug. 8, 2012, which is a continuation of U.S. patent application Ser. No. 12/604,763, filed Oct. 23, 2009, now U.S. Pat. No. 8,263,653, which is a continuation-in-part of U.S. patent application Ser. No. 12/105,100, filed, Apr. 17, 2008, which claims the benefit of and priority to U.S. Provisional Patent Application Ser. No. 60/912,605, filed Apr. 18, 2007; the entire contents of each of which are hereby incorporated by reference for all purposes.

FIELD OF THE INVENTION

The present invention is directed to pharmaceutical formulations containing lipoic acid derivatives or salts thereof which selectively kill tumor cells by altering cancer cell metabolism and signal transduction pathways linked to the Warburg Effect, as well as to methods of treating a subject with such pharmaceutical formulations.

BACKGROUND

All mammalian cells require energy to live and grow. Cells obtain this energy by metabolizing food molecules by oxidative metabolism. The vast majority of normal cells utilize a single metabolic pathway to metabolize their food. The first step in this metabolic pathway is the partial degradation of glucose molecules to pyruvate in a process known as glycolysis which yields two ATP units. Glycolysis can occur even under hypoxic conditions. Pyruvate is further degraded in the mitochondrion by a process known as the tricarboxylic acid (TCA) cycle to produce thirty-six ATP units per glucose molecule, water and carbon dioxide. The TCA cycle requires oxygen. During periods of reduced oxygen levels, normal cells adapt by a variety of mechanisms and return to normal metabolism as oxygen levels are restored. A critical link between glycolysis and the TCA cycle is an enzyme known as pyruvate dehydrogenase ("PDH"). PDH is part of a larger multi-subunit complex (hereinafter "PDC"). PDH, in conjunction with other enzymes of the PDC complex, produces acetyl CoA which effectively funnels glycolysis-produced pyruvate to the TCA cycle.

Most cancers display profound perturbation of energy metabolism. One of the fundamental changes is the adoption of the Warburg Effect, where glycolysis becomes the main source of ATP. An ATP deficit follows reduced TCA ATP generation. In other words, cancer cells behave as if they are hypoxic even when they are not. This change in energy metabolism represents one of the most robust and well-documented correlates of malignant transformation and has been linked to other changes resulting in tumor growth and metastasis. Because of the reduced levels of ATP available as a result of glycolysis largely being de-linked from the TCA cycle, cancer cells increase their uptake of glucose and its conversion to pyruvate in an attempt to make up the energy deficit. Excess pyruvate and other metabolic by-products of the Warburg biochemistry must be managed. A number of these metabolites are known to be cytotoxic, e.g., acetaldehyde. PDC in cancer along with other related enzymes plays a major role in managing and/or detoxifying the excess pyruvate and metabolites. For example, the joining of two acetyl molecules to form the neutral compound acetoin. This generation of acetoin is catalyzed by a tumor-specific form of PDC. It has been suggested that lipoic acid acts as a cofactor with PDC and related lipoamide using enzymes in detoxifying these otherwise toxic metabolites. Whether lipoic acid is made by healthy and cancer cells or whether it is an essential nutrient is debated in the literature, and both may be the case. The genes required to produce lipoic acid have been identified in mammalian cells. Whether mitochondrial pumps or uptake mechanisms are present in healthy or cancer cells or whether they differ in diverse tissues is not known. Although the TCA cycle still functions in cancer cells, the tumor cell TCA cycle is a variant cycle which depends on glutamine as the primary energy source. Inhibition or inactivation of tumor-specific PDC and related enzymes that detoxify metabolites may promote apoptosis or necrosis and cell death.

Despite extensive work characterizing the highly conserved changes among diverse tumor types and their metabolism, the changes remain to be successfully exploited as a target for cancer chemotherapy. As cancer remains the number two killer of Americans, there is an urgent need for new approaches to disease management. It has been suggested that lipoic acid due to its redox potential properties may be useful in the treatment of diverse diseases involving mitochondrial function such as diabetes, Alzheimers disease and cancer. These reports teach that the availability of the redox shift from SH to S—S be maintained to have the desired effect.

U.S. Pat. Nos. 6,331,559 and 6,951,887 disclose a novel class of therapeutic agents which selectively targets and kills tumor cells and certain other types of diseased cells. These patents further disclose pharmaceutical compositions comprising an effective amount of a lipoic acid derivative according to its invention along with a pharmaceutically acceptable carrier. However, these patents provide no specific guidance with regard to the selection of suitable pharmaceutically acceptable carriers. As the present inventors have now discovered, the pharmaceutical formulation of the lipoic acid derivatives has proved pivotal in achieving efficacy for these agents.

SUMMARY

The invention generally provides pharmaceutical formulations suited for delivering a lipoic acid derivative or salt thereof to a subject in need of treatment, such as in need of cancer treatment. The pharmaceutical formulations comprise, in certain embodiments, a pharmaceutically acceptable carrier and an ion pair formed by a lipoic acid derivative and ion pairing agent. The pharmaceutical formulations comprising the ion pair can help improve the solubility and/or efficacy of the lipoic acid derivative for use in treating, e.g., cancer. Accordingly, one aspect of the invention provides a pharmaceutical formulation comprising: (a) a pharmaceutically acceptable diluent; and (b) an ion pair formed by a lipoic acid derivative and an ion pairing agent; wherein the lipoic acid derivative is a compound of Formula I represented by:

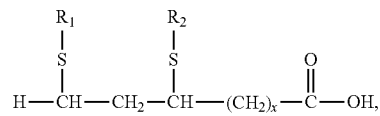

wherein the variables are as defined in the detailed description herein. In another aspect, the invention provides a pharmaceutical formulation comprising bis-benzyl lipoate, and triethanolamine. In another aspect, the invention provides an intravenous pharmaceutical composition for treating cancer, wherein the composition comprises 6,8-bis(benzylthio)octanoic acid or an ion pair thereof in an amount effective for treating cancer, and a pharmaceutically acceptable aqueous diluent for solubilizing 6,8-bis(benzylthio) octanoic acid or an ion pair thereof.

In another aspect, the invention provides a method of treating or preventing a disease characterized by disease cells that are sensitive to lipoic acid derivatives. The method comprises administering to a patient in need thereof a pharmaceutical formulation described herein to treat or prevent said disease. In certain embodiments, the disease is selected from the group consisting of carcinoma, sarcoma, myeloma, lymphoma, leukemia and mixed types thereof.

In another aspect, the invention provides a method of inducing necrotic death of a cancer cell. The method comprises administering to a cancer cell an effective amount of a pharmaceutical formulation comprising an ion pair formed by a lipoic acid derivative and an organic Bronsted base compound. In another aspect, the invention provides a method of inducing apoptotic death of a cancer cell. The method comprises administering to a cancer cell an effective amount of a pharmaceutical formulation comprising an ion pair formed by a lipoic acid derivative described herein and an ion pairing agent that is an alkali metal hydroxide or an alkaline earth metal hydroxide.

Yet another aspect of the invention provides an ion pair consisting of: at least one ion pairing agent selected from the group consisting of triethanolamine, polyethyleneimine, diethanolamine, monoethanolamine, mefenamic acid, tromethamine, ethanolamine, diethanolamine, ethylenediamine, lysine, and diethylamine; and at least one lipoic acid derivative represented by Formula (I):

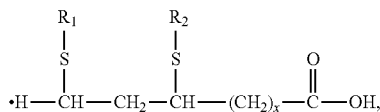

wherein the variables are as described in the detailed description.

In another aspect, the present invention is directed to a pharmaceutical formulation comprising (a) at least one lipoic acid derivative or salt thereof and (b) at least one ion pairing agent and optionally (c) a pharmaceutically acceptable diluent. In a preferred embodiment of the invention, the lipoic acid derivative has the formula (I):

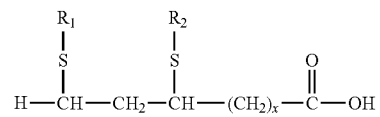

wherein $R_1$ and $R_2$ are independently selected from the group consisting of acyl defined as $R_3C(O)$—, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_3C(=NH)$—, hemiacetal defined as $R_4CH(OH)$—S—, and hydrogen provided that at least one of $R_1$ and $R_2$ is not hydrogen; wherein $R_1$ and $R_2$ as defined above can be unsubstituted or substituted; wherein $R_3$ is hydrogen, alkyl, alkenyl, alkynyl, cycloalkyl, aryl, alkylaryl, heteroaryl, or heterocyclyl, any of which can be substituted or unsubstituted; wherein $R_4$ is $CCl_3$ or COOH; and wherein x is 0-16, n is 0-10 and m is 2-10. In a preferred embodiment, $R_1$ and $R_2$ are both a benzyl group, i.e., both $R_1$ and $R_2$ are independently —$CH_2C_6H_5$. In another preferred embodiment, the lipoic acid derivative has the formula (II):

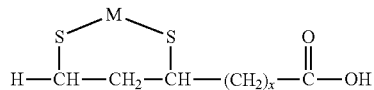

wherein M is a metal chelate, —$[C(R_1)(R_2)]_z$— or other metal complex; wherein $R_1$ and $R_2$ are independently selected from the group consisting of acyl defined as $R_3C(O)$—, alkyl defined as $C_nH_{2n+1}$, alkenyl defined as $C_mH_{2m-1}$, alkynyl defined as $C_mH_{2m-3}$, aryl, alkyl sulfide defined as $CH_3(CH_2)_n$—S—, imidoyl defined as $R_3C(=NH)$—, hemiacetal defined as $R_4CH(OH)$—S— and hydrogen; wherein $R_1$ and $R_2$ as defined above can be unsubstituted or substituted; wherein $R_3$ is hydrogen, alkyl, alkenyl, alkynyl, cycloalkyl, aryl, alkylaryl, heteroaryl, or heterocyclyl, any of which can be substituted or unsubstituted; wherein $R_4$ is $CCl_3$ or COOH; and wherein x is 0-16, z is 0-5, n is 0-10 and m is 2-10.

Further preferred embodiments of this invention include those in which the lipoic acid derivative is present in a therapeutically effective amount. Still further preferred embodiments of this invention include those in which the ion pairing agent is selected from the group consisting of triethanolamine, polyethyleneimine, monoethanolamine, diethanolamine, mefenamic acid, tromethamine and combinations thereof, those in which the ion pairing agent is a polymer-conjugated ion pairing agent, and those in which the ion pairing agent and the at least one lipoic acid derivative is present in a ratio ranging from about 1000:1 to about 1:1000. Further preferred embodiments of the present invention also include those in which the diluent is selected from the group consisting of saline, a sugar solution, an alcohol, dimethylformamide, dimethylsulfoxide, dimethylacetamide and combinations thereof.

In another aspect, the present invention is directed to a method of treating a disease characterized by disease cells that are sensitive to lipoic acid derivatives comprising administering to a patient in need thereof a pharmaceutical formulation comprising at least one lipoic acid derivative or salt thereof, at least one ion pairing agent, and optionally a pharmaceutically acceptable diluent. In yet another aspect, the present invention is directed to a method of preventing a disease characterized by disease cells that are sensitive to lipoic acid derivatives comprising administering to a patient in need thereof a pharmaceutical formulation comprising at least one lipoic acid derivative, at least one ion pairing agent, and optionally a pharmaceutically acceptable diluent. In preferred embodiments of these methods, the disease is a cancer such as a carcinoma, sarcoma, myeloma, lymphoma, leukemia, or a mixed cancer type.

In yet another aspect, the invention is directed to an ion pair consisting of (a) at least one lipoic acid derivative and (b) at least one ion pairing agent, most preferably bis-benzyl lipoate and triethanolamine, respectively.

BRIEF DESCRIPTION OF THE FIGURES

FIGS. 2A, 2B and 2C show the tumor volume in H-460 tumor-bearing mice treated with bis-benzyl lipoate in a triethanolamine/dextrose pharmaceutical formulation at 3 different dosage levels.

DETAILED DESCRIPTION

Figures 1A, 1B:
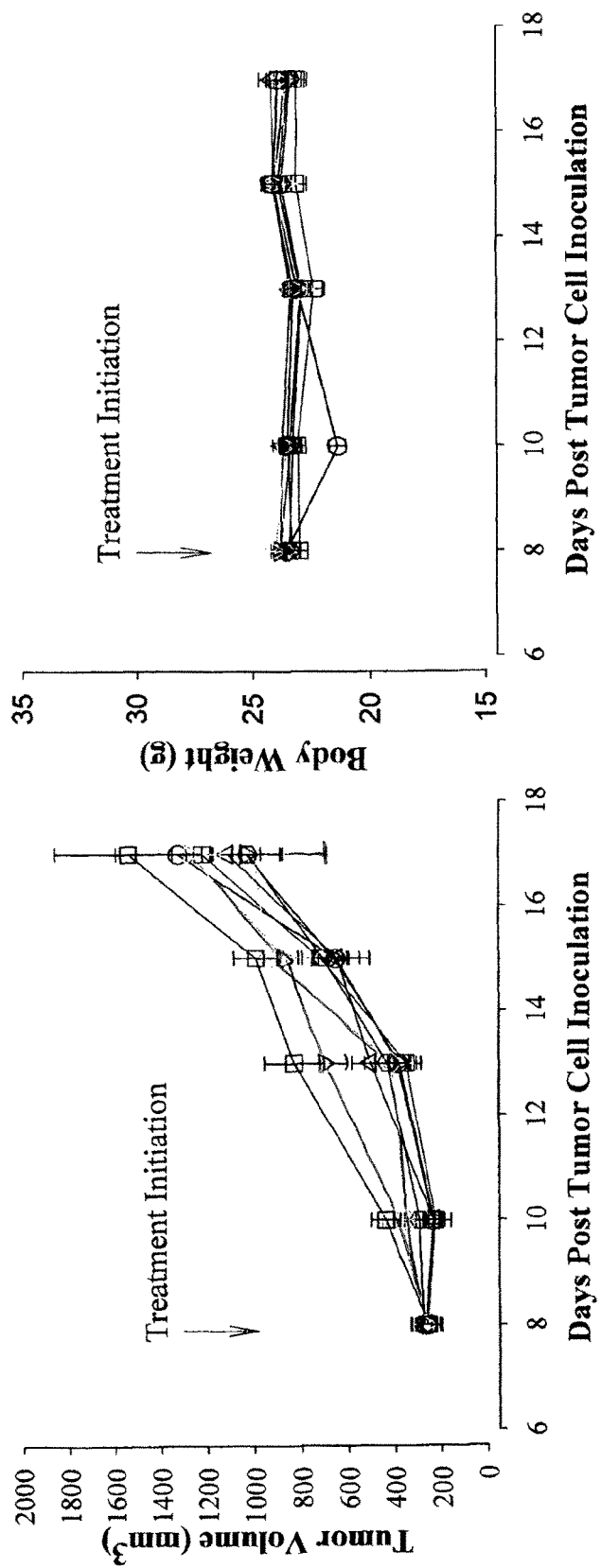
FIGS. 1A and 1B show the tumor volume and body weight, respectively, in H-460 tumor-bearing mice treated with bis-benzyl lipoate in a Tween 80/ethanol pharmaceutical formulation.
Figure 3:
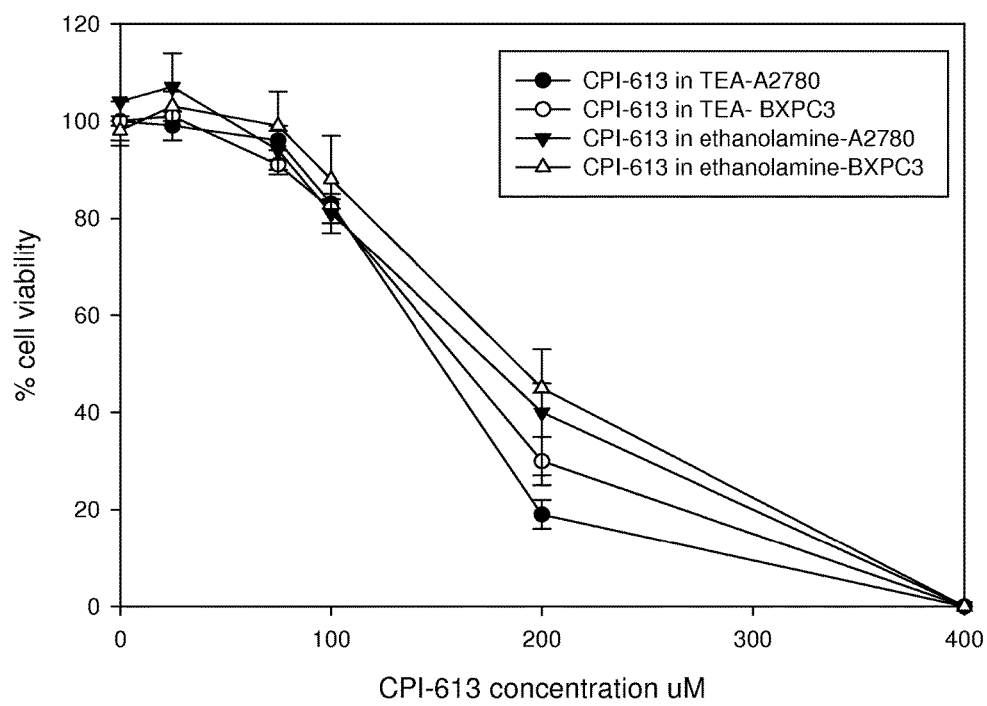
FIG. 3 shows percent viability of A2780 and BXPC3 tumor cells treated with either CPI-613 in triethanolamine or CPI-613 in ethanolamine.
Figure 4:
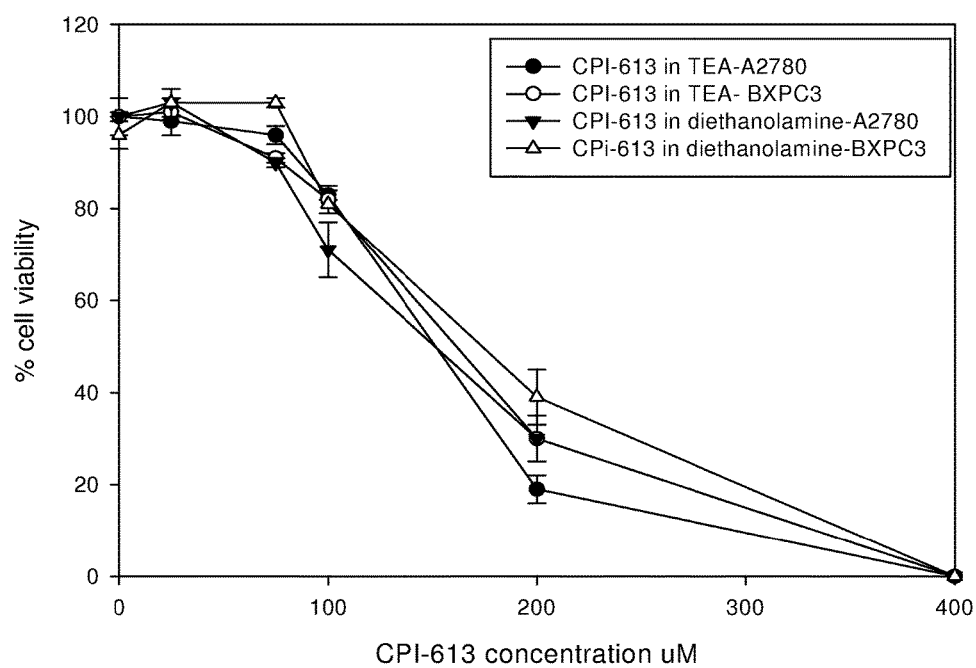
FIG. 4 shows percent viability of A2780 and BXPC3 tumor cells treated with either CPI-613 in triethanolamine or CPI-613 in diethanolamine.
Figure 5:
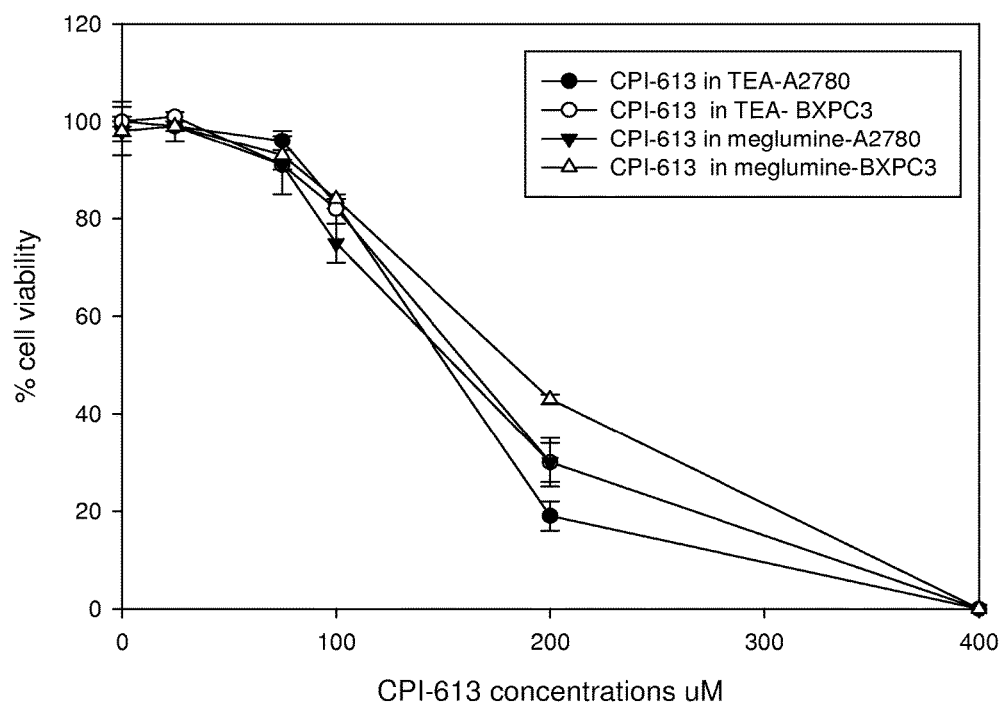
FIG. 5 shows percent viability of A2780 and BXPC3 tumor cells treated with either CPI-613 in triethanolamine or CPI-613 in meglumine.
Figure 6:
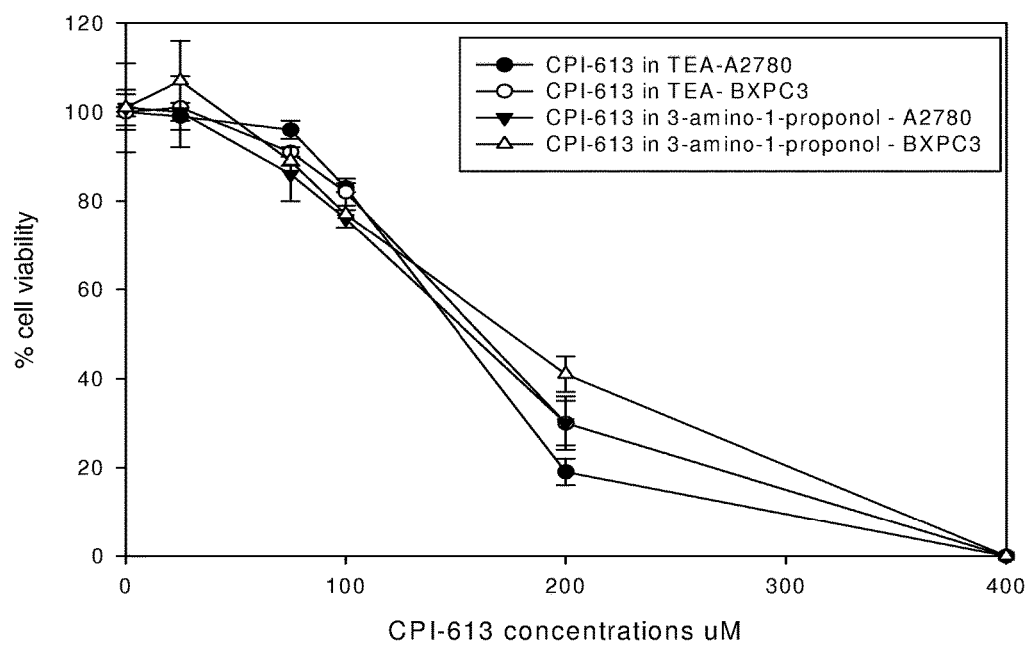
FIG. 6 shows percent viability of A2780 and BXPC3 tumor cells treated with either CPI-613 in triethanolamine or CPI-613 in 3-amino-1-propanol.
Figure 7:
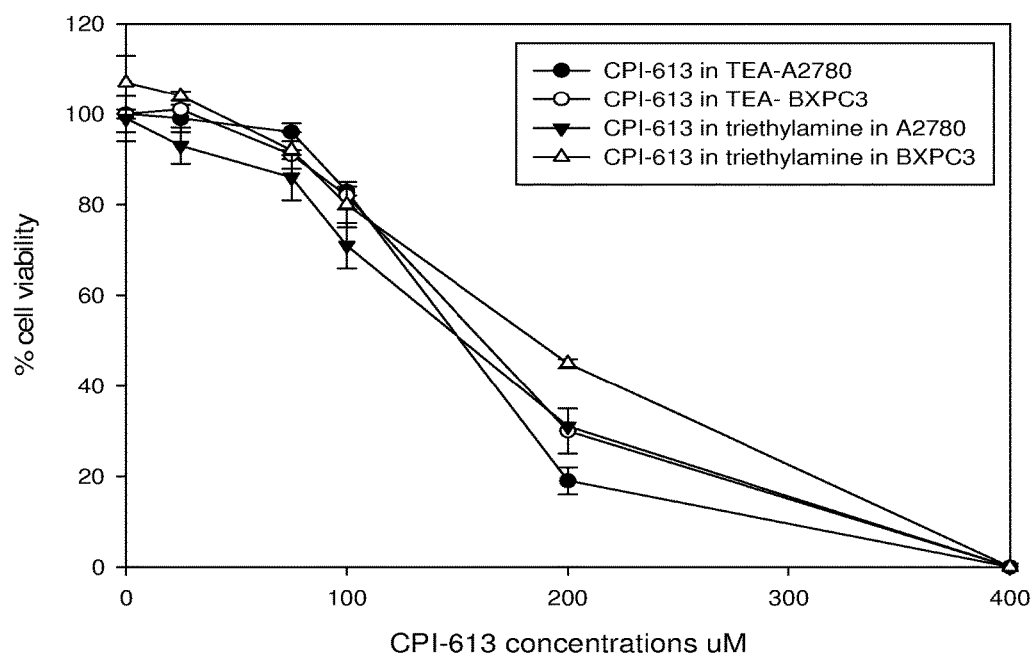
FIG. 7 shows percent viability of A2780 and BXPC3 tumor cells treated with either CPI-613 in triethanolamine or CPI-613 in triethylamine.
Figure 8:
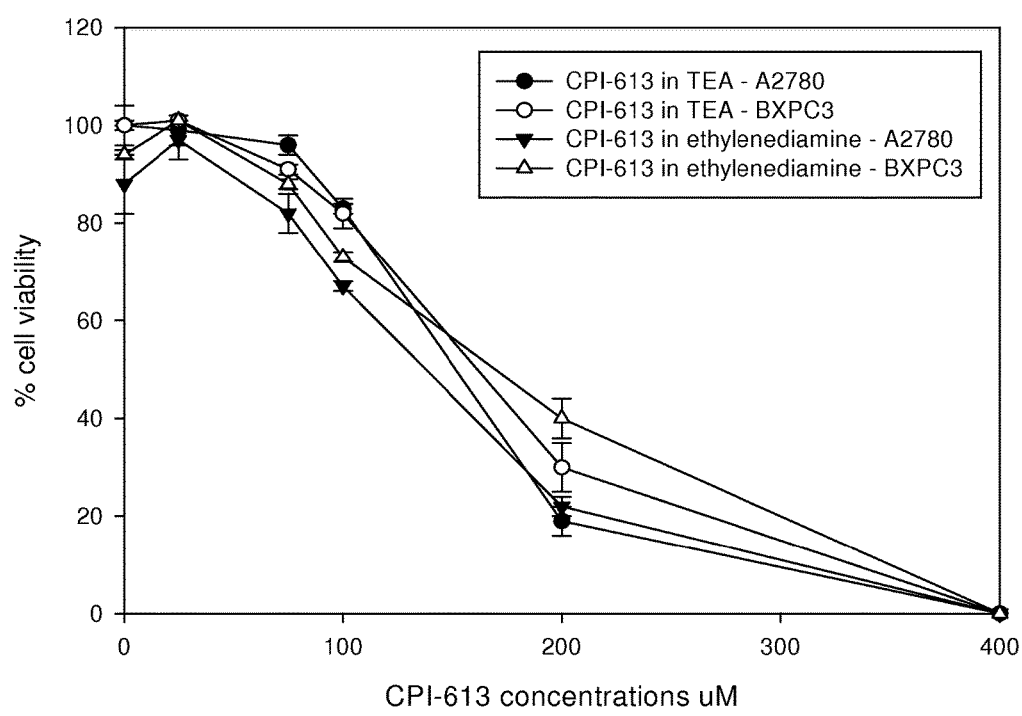
FIG. 8 shows percent viability of A2780 and BXPC3 tumor cells treated with either CPI-613 in triethanolamine or CPI-613 in ethylenediamine.
Figure 9:
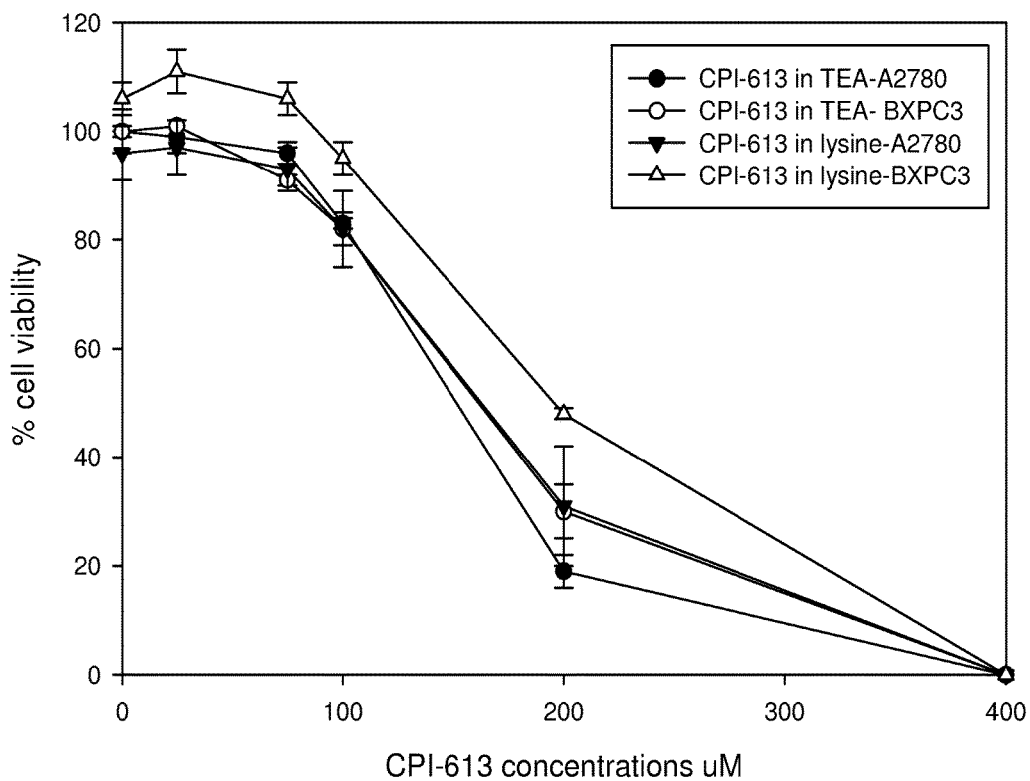
FIG. 9 shows percent viability of A2780 and BXPC3 tumor cells treated with either CPI-613 in triethanolamine or CPI-613 in lysine.
Figure 10:
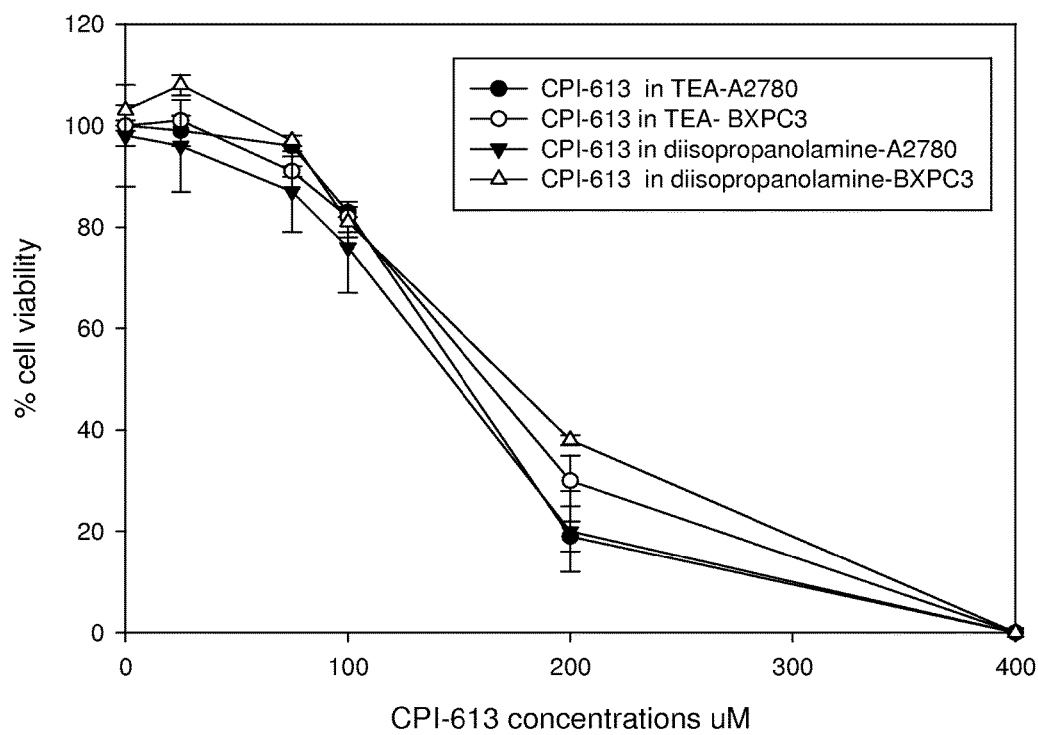
FIG. 10 shows percent viability of A2780 and BXPC3 tumor cells treated with either CPI-613 in triethanolamine or CPI-613 in diisopropanolamine.
Figure 11:
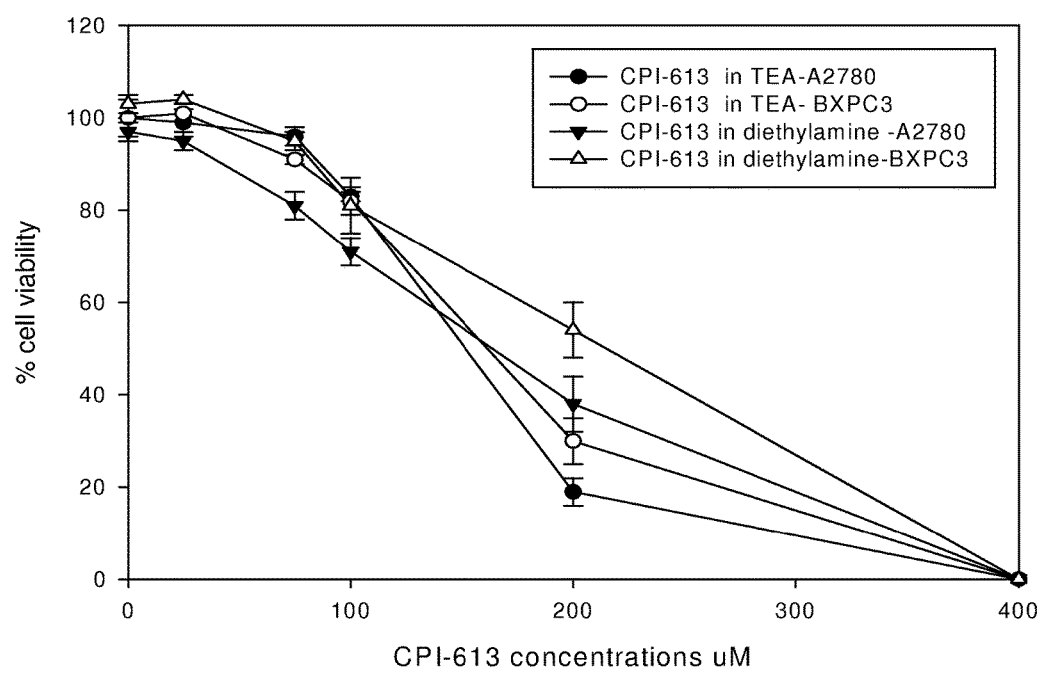
FIG. 11 shows percent viability of A2780 and BXPC3 tumor cells treated with either CPI-613 in triethanolamine or CPI-613 in diethylamine.

The present invention is directed to pharmaceutical formulations containing lipoic acid derivatives which are effective to target and kill tumor cells. While the pharmaceutical formulation of many therapeutic agents is quite conventional, the present inventors have found that the pharmaceutical formulation of lipoic acid derivatives is not. In fact, the particular pharmaceutical formulation in which a lipoic acid derivative is placed may well be the determining factor between inactivity and activity for its intended purpose. Accordingly, one aspect of the invention provides a pharmaceutical formulation comprising (a) at least one lipoic acid derivative and (b) at least one ion pairing agent and optionally (c) a pharmaceutically acceptable diluent, as described in detail herein.

I. Lipoic Acid Derivatives and Ion Pairs Thereof

Lipoic acid derivatives suitable for use in the present invention include those described in full detail in each of U.S. Pat. Nos. 6,331,559 and 6,951,887 and those described in U.S. Provisional Application No. 60/912,598, filed Apr. 18, 2007 and corresponding co-pending U.S. patent application Ser. No. 12/105,096, filed Apr. 18, 2008, the disclosure of each of which is incorporated by reference herein. Lipoic acid derivatives suitable for use in the present invention can be made according to known procedures such as those set forth in the aforementioned patents. In a preferred embodiment of this invention, the lipoic acid derivative has the formula (I):

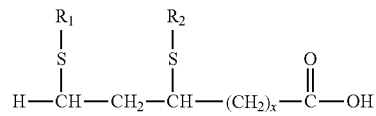

or a salt thereof;

wherein $R_1$ and $R_2$ are independently selected from the group consisting of acyl defined as $R_3C(O)$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_3C(=NH)$—, hemiacetal defined as $R_4CH(OH)$—S—, and hydrogen provided that at least one of $R_1$ and $R_2$ is not hydrogen;

wherein $R_1$ and $R_2$ as defined above can be unsubstituted or substituted;

wherein $R_3$ is hydrogen, alkyl, alkenyl, alkynyl, cycloalkyl, aryl, alkylaryl, heteroaryl, or heterocyclyl, any of which can be substituted or unsubstituted;

wherein $R_4$ is $CCl_3$ or COOH; and wherein x is 0-16, n is 0-10 and m is 2-10.

As used herein, acyl refers to an $R_3C(O)$— group, where $R_3$ can be, without limitation, hydrogen, alkyl, alkenyl, alkynyl, cycloalkyl, aryl, alkylaryl, heteroaryl, or heterocyclyl, any of which can be substituted or unsubstituted. In other words, one of the listed $R_3$ groups is linked to the carbon backbone of formula (I) through a thio-ester linkage. Examples of acyl groups include, without limitation, acetyl, benzoyl and benzoyl derivatives, 4-fluorobenzoyl and 1-methylpyrrole-2-carboxyl. Specific examples of lipoic acid derivatives containing an acyl group include, without limitation, bis-acetyl lipoate and bis-benzoyl lipoate.

As used herein, alkyl refers to a $C_nH_{2n+1}$ group, wherein n is 1-10, more preferably 1-6 and most preferably 1-4, i.e., an alkyl group linked to the carbon backbone of formula (I) through a thio-ether linkage. Alkyl groups can be either aliphatic (straight or branched chain) or alicyclic; alicyclic groups may have additions or substitutions on any of the carbons to form heterocyclics. At least one heteroatom such as N, O or S may be present in a given alkyl group, i.e., in the carbon chain. Alkyl groups may be substituted or unsubstituted on any of their carbons. A preferred alkyl group is an alkyl group substituted with an aryl or heteroaryl group, i.e., wherein $R_1$ or $R_2$ is an alkylaryl or alkylheteroaryl group; the aryl or heteroaryl group may be substituted or unsubstituted. Examples of alkyl groups include, without limitation, methyl, ethyl, butyl, decanyl, cyclopropyl, 4-pyridine methyl, 2-anthraquinone methyl, N-phenylacetamide, phenylethyl, 2-ethanoic acid, 2-acetamido, 4-(2-acetamido-pyridinyl)methyl, N-[(2-fluorophenyl)methyl]acetamide, N-[(6-methoxy-3-pyridyl)methyl]acetamide, 5-(acetylamino)pyridine-2-carboxamide, 5-(6,8-diaza-7-oxo-3-thiabicyclo[3.3.0]oct-2-yl)-N-(2-carbonylamino-ethyl)pentanamide and 5-(6,8-diaza-7-oxo-3-thiabicyclo[3.3.0]oct-2-yl)pentacarboxyl. Specific examples of lipoic acid derivatives containing an alkyl group include, without limitation, 6,8-bis carbamoyl methylipoate and 6,8 methyl-succinimido lipoate.

As used herein, alkenyl refers to a $C_mH_{2m-1}$ group, wherein m is 2-10, i.e., an alkenyl group linked to the carbon backbone of formula (I) through a thio-ether linkage. Alkenyl groups can be either aliphatic (straight or branched chain) or alicyclic; alicyclic groups may have additions or substitutions on any of the carbons to form heterocyclics. At least one heteroatom such as N, O or S may be present in a given alkenyl group, i.e., in the carbon chain. Alkenyl groups may be substituted or unsubstituted on any of their carbons. Examples of alkenyl groups include, without limitation, propenyl, 2,3 dimethyl-2-butenyl, heptenyl and cyclopentenyl.

As used herein, alkynyl refers to a $C_mH_{2m-3}$, where m is 2-10, i.e., an alkynyl group linked to the carbon backbone of formula (I) through a thio-ether linkage. Alkynyl groups can be either aliphatic (straight or branched chain) or alicyclic; alicyclic groups may have additions or substitutions on any of the carbons to form heterocyclics. At least one heteroatom such as N, O or S may be present in a given alkynyl group, i.e., in the carbon chain. Alkynyl groups may be substituted or unsubstituted on any of their carbons. Examples of alkynyl groups include, without limitation, acetylenyl, propynyl and octynyl.

As used herein, aryl refers to an aromatic or aryl group linked to the carbon backbone of formula (I) through a thio-ether linkage. Aryl is preferably an unsaturated ring system having 6-10 carbon atoms. Aryl also includes organometallic aryl groups such as ferrocene. Aryl groups may be substituted or unsubstituted on any of their carbons. Examples of aryl groups include, without limitation, benzyl ($-CH_2C_6H_5$), benzyl derivatives such as methylbenzyl and aminobenzyl, (1,2,3,4,5-pentafluorophenyl)methyl, triphenylmethyl, 4-methy benzoic acid, ferrocene methyl, 2-naphthylmethyl, 4,4-biphenylmethyl, and stilbene (or 1-((1E)-2-phenylvinyl)-4-methyl benzene). A specific example of a lipoic acid derivative containing an aryl group is bis-benzyl lipoate.

As used herein, heteroaryl refers to an aromatic heterocyclic ring system (monocyclic or bicyclic) where the heteroaryl moieties are five or six membered rings containing 1 to 4 heteroatoms selected from the group consisting of S, N, and O; the heteroaryl group is linked to the carbon backbone of formula (I) through a thio-ether linkage. Heteroaryl groups may be substituted or unsubstituted on any of their atoms especially on the carbon atoms. Examples of heteroaryl groups include, without limitation, benzothiazole, quinoline, 7-chloroquinoline, furan, thiophene, indole, azaindole, oxazole, thiazole, isoxazole, isothiazole, imidazole, N-methylimidazole, pyridine, pyrimidine, pyrazine, pyrrole, N-methylpyrrole, pyrazole, N-methylpyrazole, 1,3, 4-oxadiazole, 1,2,4-triazole, 1-methyl-1,2,4-triazole, 1H-tetrazole, 1-methyltetrazole, benzoxazole, benzofuran, benzisoxazole, benzimidazole, N-methylbenzimidazole, azabenzimidazole, indazole, quinazoline and pyrrolidinyl.

As used herein, alkyl sulfide refers to a $CH_3(CH_2)_n-S-$ group, where n is 0-9. In other words, an alkyl group is linked to the carbon backbone of formula (I) through a disulfide linkage. The alkyl group (i.e., $CH_3(CH_2)_n$) can be substituted or unsubstituted on any of its carbons and shares the same features as set forth above with regard to the $C_nH_{2n+1}$ alkyl group.

As used herein, imidoyl refers to a $R_3C(=NH)-$ group, where $R_3$ can be, without limitation, hydrogen, alkyl, alkenyl, alkynyl, cycloalkyl, aryl, alkylaryl, heteroaryl, or heterocyclyl, any of which can be substituted or unsubstituted. In other words, one of the listed $R_3$ groups is linked to the carbon backbone of formula (I) through a thio-imide linkage.

As used herein, hemiacetal refers to an $R_4CH(OH)-S-$ group, where $R_4$ is a compound with strongly electron withdrawing substituents such as, without limitation, $CF_3$, $CCl_3$ or COOH.

Any of the above-described groups can be unsubstituted or substituted. Exemplary substituents include, without limitation, alkyl, alkenyl, alkynyl, aryl, heteroaryl, acyl, alkoxycarbonyl, alkoxy, alkoxyalkyl, alkoxyalkoxy, cyano, halogen, hydroxy, nitro, oxo, trifluoromethyl, trifluoromethoxy, trifluoropropyl, amino, amido, alkylamino, dialkylamino, dialkylaminoalkyl, hydroxyalkyl, alkoxyalkyl, alkylthio, $-SO_3H$, $-SO_2NH_2$, $-SO_2NHalkyl$, $-SO_2N(alkyl)_2$, $-CO_2H$, $CO_2NH_2$, $CO_2NHalkyl$, and $-CO_2N(alkyl)_2$. In addition, any number of substitutions may be made on any of the above-described groups; in other words, it is possible to have a mono-, di-, tri-, etc. substituted $R_1$ or $R_2$ group, and the substituents themselves may also be substituted. Further, any of the $R_1$ or $R_2$ groups may be appropriately generally substituted with any of a carbohydrate, a lipid, a nucleic acid, an amino acid or a polymer of any of those, or a single or branched chain synthetic polymer (having a molecular weight ranging from about 350 to about 40,000).

For any definition of $R_1$ and $R_2$ noted above, the thio-ester or thio-ether linkage by which the $R_1$ and $R_2$ are linked to the backbone can be oxidized to produce sulfoxides or sulfones; in other words, the $-S-$ in the linkage could be $-S(O)-$ or $-S(O)_2$. In addition, for any definition of $R_1$ and $R_2$ noted above, the thio-ester or thio-ether linkage by which the $R_1$ and $R_2$ are linked to the backbone may further comprise disulfides that can be oxidized to thiosulfinic or thiosulfonic acids; in other words, instead of $-S-$ in a linkage, the linkage could be $-S(O)-S-$ or $-S(O)_2-S-$.

In another preferred embodiment of this invention, the lipoic acid derivative has the formula (II):

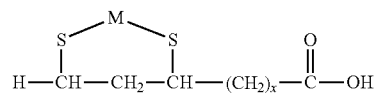

M is a metal chelate, $-[C(R_1)(R_2)]_z-$ or other metal complex. $R_1$ and $R_2$ are independently selected from the group consisting of acyl defined as $R_3C(O)-$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n-S-$, imidoyl defined as $R_3C(=NH)-$, hemiacetal defined as $R_4CH(OH)-S-$ and hydrogen, wherein $R_1$ and $R_2$ as defined above can be unsubstituted or substituted. $R_3$ is hydrogen, alkyl, alkenyl, alkynyl, cycloalkyl, aryl, alkylaryl, heteroaryl, or heterocyclyl, any of which can be substituted or unsubstituted; $R_4$ is $CCl_3$ or COOH. In addition, x is 0-16, z is preferably 0-5, more preferably 0-3, n is 0-10 and m is 2-10. Suitable —[C(R₁)(R₂)]z— groups include, without limitation, —CH₂, —CH(CH₃), —C(CH₃)₂, —CH(C₆H₅) and —CH(pyridine).

Also in this embodiment, a metal or metal salt can be added to one or both sulfhydryls through a bond in which a metal or metal salt forms a covalent or coordination or chelated complex with the thiol group(s) of the lipoic acid molecule. Such metals include, platinum, nickel, silver, rhodium, cadmium, gold, palladium or cobalt. Metal salts include, for example, platinum bromide, platinum chloride, platinum iodide, nickel borate, nickel boride, nickel bromide, nickel chloride, nickel iodide, nickel fluoride, silver bromate, silver bromide, silver chloride, silver fluoride, silver iodide, rhodium chloride, cadmium bromide, cadmium chloride, cadmium fluoride, cadmium iodide, gold bromide, gold chloride, gold iodide, cobalt bromide, cobalt bromide, cobalt chloride, cobalt fluoride, cobalt iodide, palladium chloride, palladium iodide, and palladium bromide. Such salts include various metal oxidation states such as, for example, platinum (II) chloride and platinum (IV) chloride. In general, the structure of the lipoic acid-metal complex described herein is likely to be (metal)$_n$, (lipoic acid)$_n$ where m and n are both one or where m is one and n is two.

Regardless of whether the lipoic acid derivative is of formula (I) or formula (II), pharmaceutical formulations of the present invention may include lipoic acid derivatives in which one or both of the thiols have been replaced with a selenium molecule, a sulfur analog, or in which one or both of the thiols have been oxidized to sulfate or related groups.

In particularly preferred embodiments of the present invention, the lipoic acid derivative is one selected from the following:

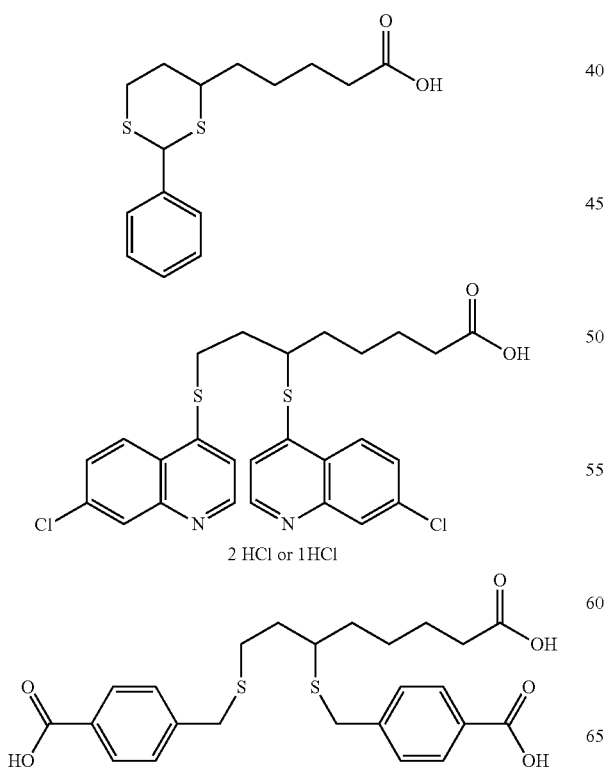

2 HCl or 1HCl

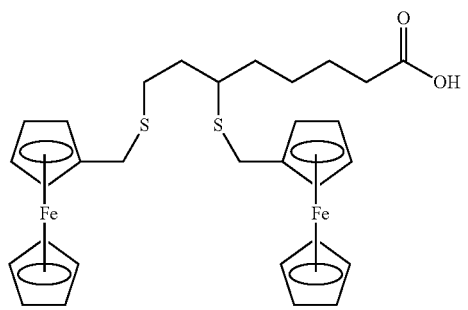

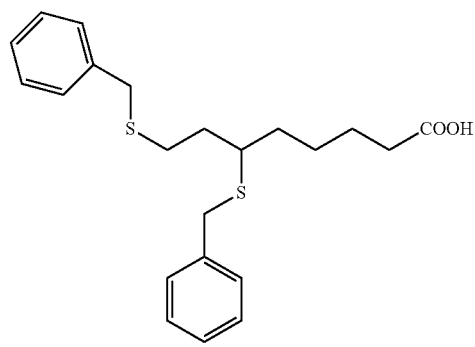

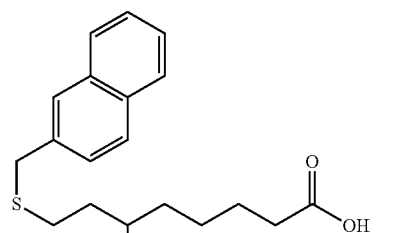

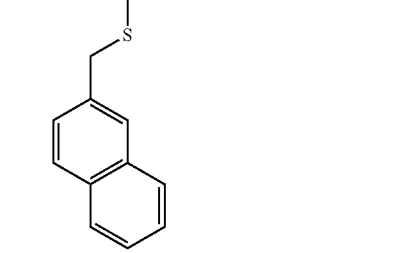

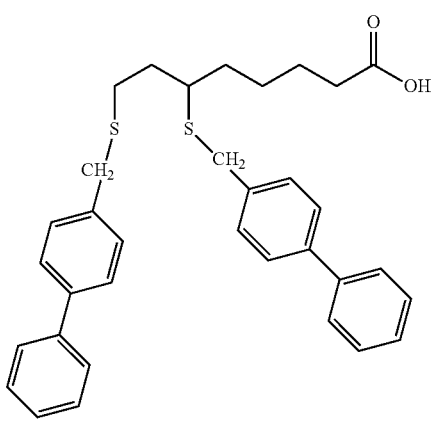

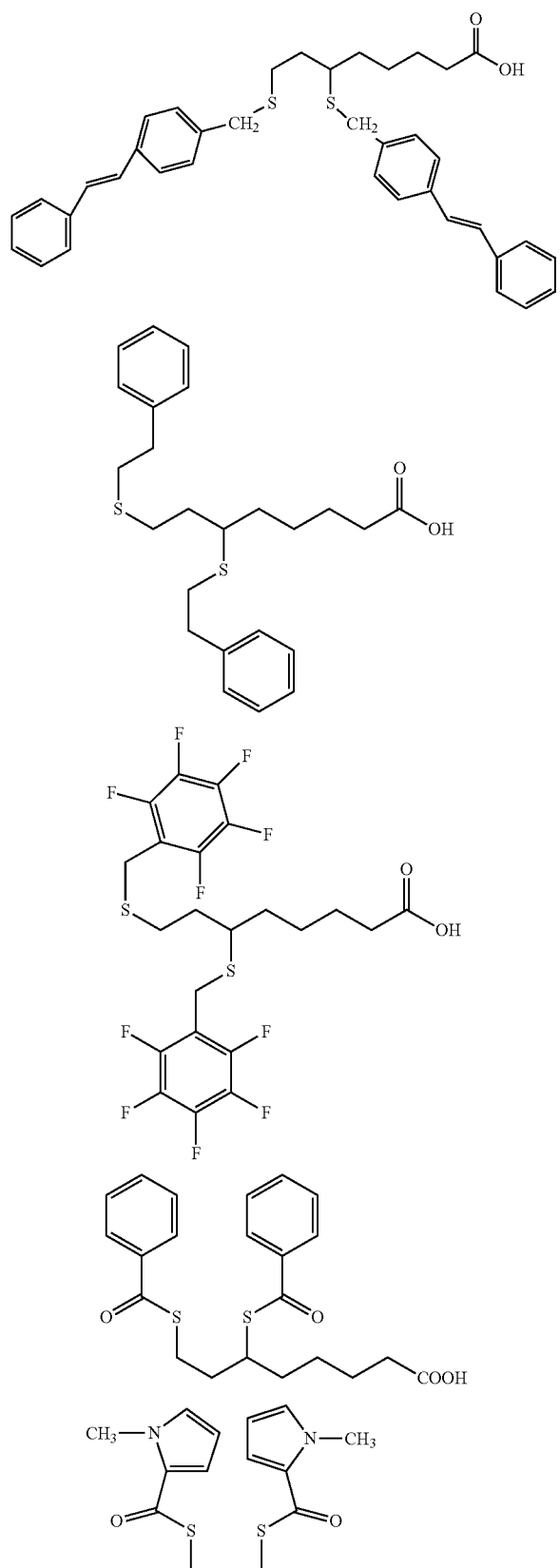
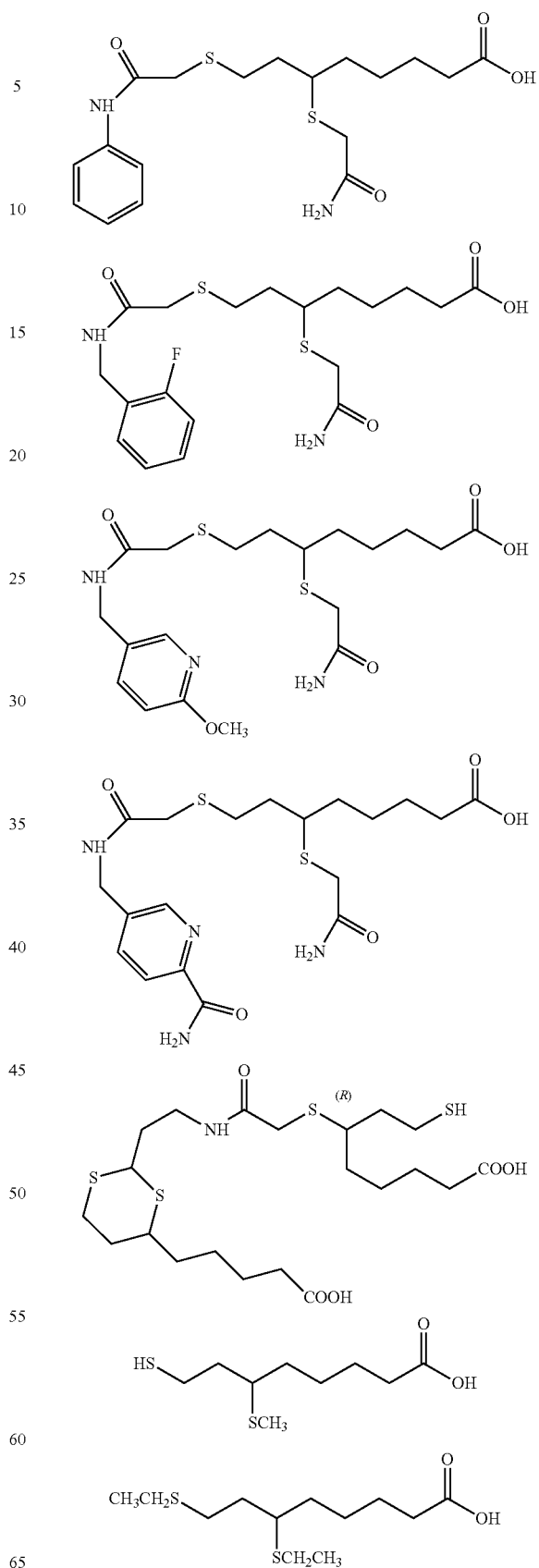

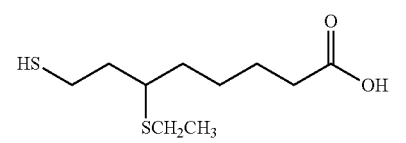
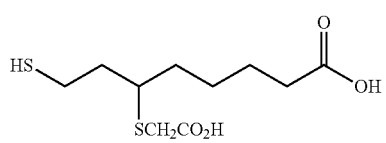
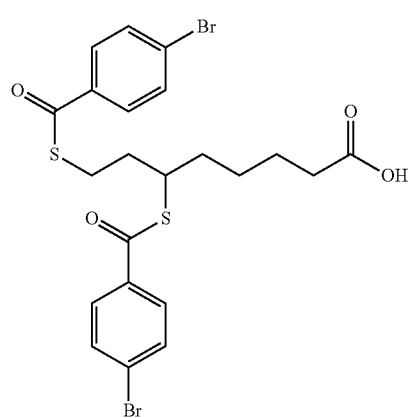
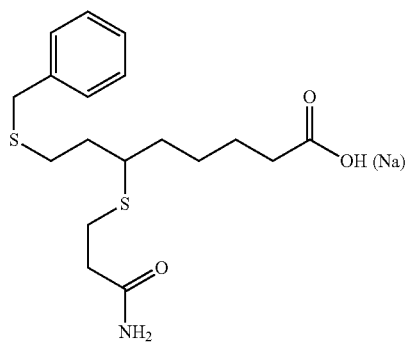
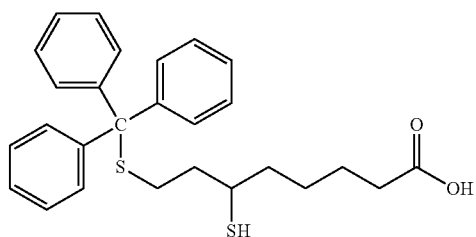
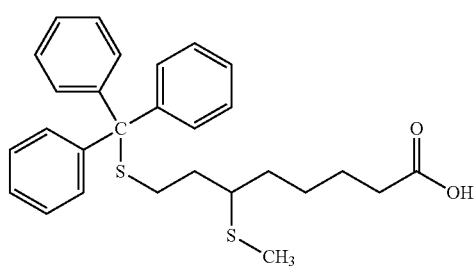
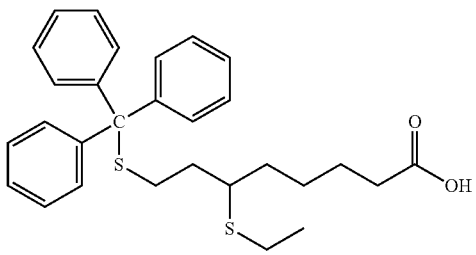
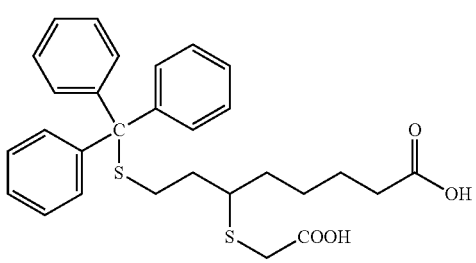
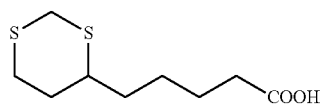
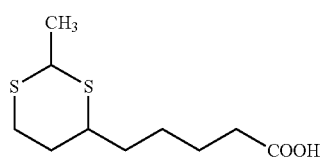
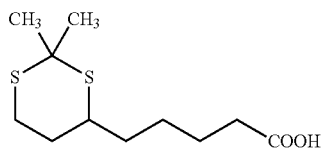
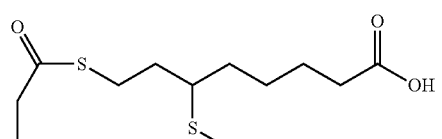
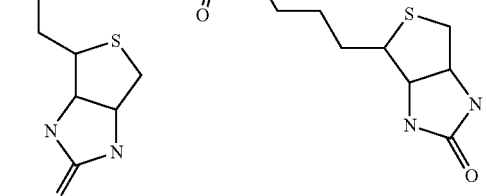
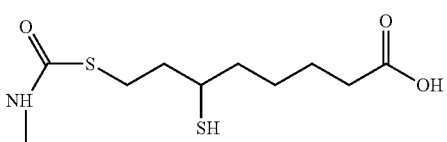
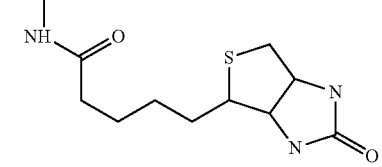

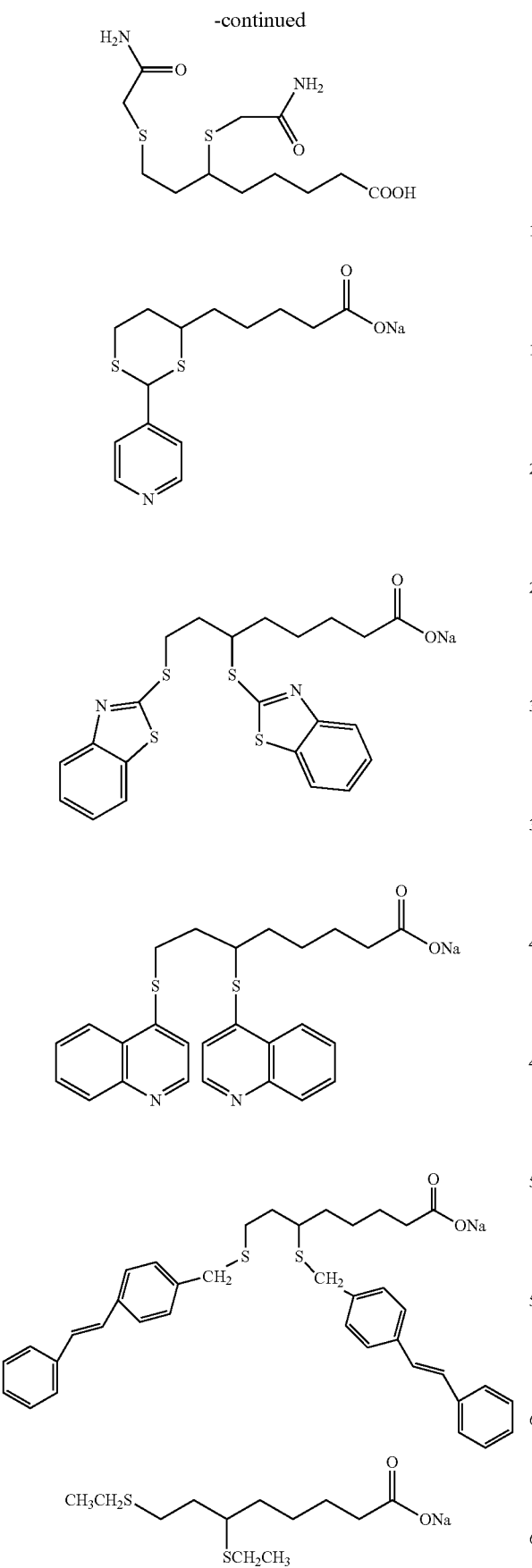
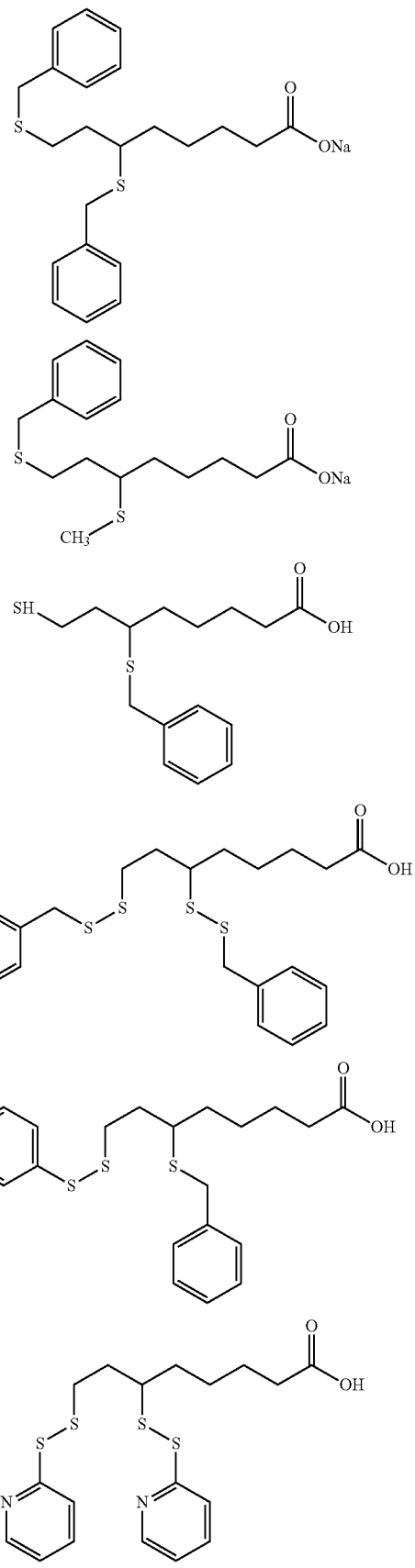

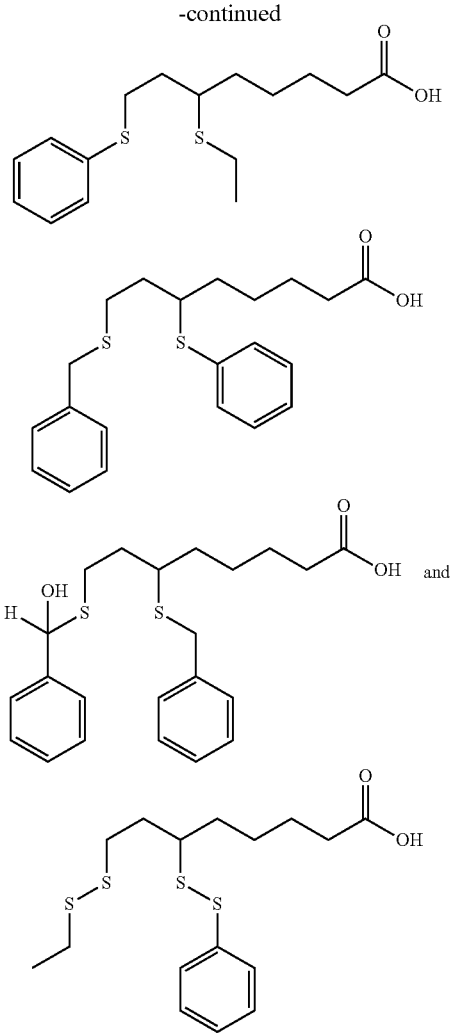

or a salt thereof (if not already in salt form).

Certain compounds described herein may exist in particular geometric or stereoisomeric forms. The present invention contemplates all such compounds, including cis- and trans-isomers, R- and S-enantiomers, diastereomers, (D)-isomers, (L)-isomers, racemic mixtures thereof, diastereomeric mixtures thereof, and other mixtures thereof, as falling within the scope of the invention. Further, unless specifically indicated otherwise, generic chemical structures presented herein are intended to encompass all geometric or stereoisomeric forms.

When the at least one lipoic acid derivative is a salt, it may be necessary to perform ion exchange in order to achieve ion pairing in accordance with the invention. However, if a weak salt is used, an ion pairing agent such as triethanolamine could displace the anion without the need for ion exchange.

Typically the at least one lipoic acid derivative is present in a pharmaceutical formulation of the present invention in a therapeutically effective amount. The pharmaceutical formulation of the present invention may contain a unit dose or multiple doses of the lipoic acid derivative. A "therapeutically effective amount" is intended to mean the amount of a lipoic acid derivative that, when administered to a subject in need thereof, is sufficient to effect treatment for (or prevent) disease conditions characterized by disease cells that are sensitive to lipoic acid derivatives. The amount of a given lipoic acid derivative that will be therapeutically effective will vary depending upon factors such as the disease condition and the severity thereof, the identity of the subject in need thereof, etc., which amount may be routinely determined by those of ordinary skill in the art. Importantly, the quantity of lipoic acid derivative in a unit dose should be sufficient to inhibit or kill tumor cells while leaving normal cells substantially unharmed. The at least one lipoic acid derivative is preferably present in a pharmaceutical formulation of the present invention in an amount to provide from about 0.001 mg/m$^2$ to about 10 g/m$^2$, more preferably about 0.01 mg/m$^2$ to about 5 g/m$^2$, still more preferably from about 0.25 mg/m$^2$ to about 3 g/m$^2$, and most preferably from about 20 mg/m$^2$ to about 500 mg/m$^2$ of the at least one lipoic acid derivative per dose. In certain other embodiments, the at least one lipoic acid derivative is present in a pharmaceutical formulation of the present invention in an amount to provide from about 20 mg/m$^2$ to about 2500 mg/m$^2$, about 300 mg/m$^2$ to about 700 mg/m$^2$, about 400 mg/m$^2$ to about 600 mg/m$^2$, about 380 mg/m$^2$ to about 450 mg/m$^2$, about 410 mg/m$^2$ to about 430 mg/m$^2$, about 500 mg/m$^2$ to about 700 mg/m$^2$, about 550 mg/m$^2$ to about 650 mg/m$^2$, or about 580 mg/m$^2$ to about 600 mg/m$^2$ of the at least one lipoic acid derivative per dose.

Importantly, the pharmaceutical formulations of the present invention includes at least one ion pairing agent. As used herein, "ion pairing agent" refers to any agent which is capable of forming a "salt bridge" or an "ion pair" with a given lipoic acid derivative. As used herein, "salt bridge" or "ion pair" refers to not only a salt (weak or strong) formed between an ion pairing agent and a given lipoic acid derivative, but also to other ionic associations (weak or strong) that do not rise to the level of actual salt formation between an ion pairing agent and a given lipoic acid derivative. Without being bound by theory, it is believed that an ion pairing agent such as triethanolamine forms a salt bridge, i.e., forms a salt in situ, with a lipoic acid derivative such as bis-benzyl lipoate, which then enables the lipoic acid deriviative to achieve its cell kill effect in vivo.

Ion pairing agents particularly suitable for use in the present invention include, without limitation, tertiary amines such as triethanolamine and polyethyleneimine, other amines such as diethanolamine, monoethanolamine, mefenamic acid and tromethamine, and combinations thereof. A preferred ion pairing agent is triethanolamine. In certain embodiments, the ion pairing agent is an organic Bronsted base. In certain other embodiments, the ion pairing agent is an amine compound. In certain preferred embodiments, the ion pairing agent is a monoalkylamine, dialkylamine, trialkylamine, amino-substituted aliphatic alcohol, hydroxymonoalkylamine, hydroxydialkylamine, hydroxytrialkylamine, amino-substituted heteroaliphatic alcohol, alkyldiamine, substituted alkyldiamine, or optionally substituted heteroaryl group containing at least one ring nitrogen atom.

Additional ion pairing agents suitable for use in this invention include polymer-conjugated ion pairing agents which employ, without limitation, polyethylene glycol, polyethyleneimine, polyglutamic acid and sugar-based polymers such as dextrans in combination with any of the above-noted ion pairing agents or any other known ion pairing agent. Still further ion pairing agents can be selected with guidance from Handbook of Pharmaceutical Salts: Properties, Selection and Use, IUPAC, Wiley-VCH, P. H. Stahl, ed., the entire disclosure of which is incorporated by reference herein. Ion pairing agents of particular note therein include, without limitation, those listed in Table 5, p. 342, i.e., ammonia, L-arginine, benethamine benzathine, betaine, calcium hydroxide, choline, deanol, diethanolamine(2,2'-iminobis(ethanol)), diethylamine, 2-(diethylamino)-ethanol, ethanolamine, ethylenediamine, N-methyl-glucamine, hydrabamine, 1H-imidazole, lysine, magnesium hydroxide, 4-(2-hydroxyethyl)-morpholine, piperazine, potassium hydroxide, 1-(2-hydroxyethyl)-pyrrolidine, sodium hydroxide, triethanolamine (2,2',2"-nitrilotris(ethanol)), tromethamine, and zinc hydroxide. In certain other embodiments, the ion pairing agent is diisopropanolamine, 3-amino-1-propanol, meglumine, morpholine, pyridine, niacinamide, tris(hydroxymethyl)aminomethane, 2-((2-dimethylamino)ethoxy)ethanol, 2-(dimethylamino)ethanol, 1-(2-hydroxyethyl)pyrrolidine, or ammonium hydroxide. In certain other embodiments, the ion pairing agent is an alkali metal hydroxide or alkaline earth metal hydroxide, such as, for example, cesium hydroxide.

The ion pairing agent may be hydrophilic or hydrophobic (such as acylated triethanolamine). Typically the ion pairing agent is present in an amount sufficient to achieve substantial solubility of the at least one lipoic acid derivative in a solvent suitable for intravenous administration, which is most preferably an aqueous medium. Preferably the ion pairing agent and lipoic acid derivative are present in a molar ratio ranging from about 1000:1 to about 1:1000, more preferably from about 500:1 to about 1:500, still more preferably from about 50:1 to about 1:50, still further more preferably from about 20:1 to about 1:20, and most preferably of about 1:1. In certain other embodiments, the molar ratio of ion pairing agent to lipoic acid derivative is about 1:1 to about 10:1, or about 5:1 to about 10:1, or about 8:1.

Yet another embodiment of the present invention is directed to an ion pair, be it a true salt or some other lesser ionic association, consisting of (a) at least one lipoic acid derivative and (b) an ion pairing agent. In a highly preferred embodiment, the ion pair consists of bis-benzyl lipoate and triethanolamine. The present invention includes all ion pairs, whether in situ as formed or isolated by some conventional method. All of the details regarding amounts of (a) and (b) and possible materials suitable for use are the same as those set forth in the general description above. Further, in certain embodiments, the invention provides an ion pair consisting of, or in certain instances consisting essentially of:

(a) at least one ion pairing agent selected from the group consisting of triethanolamine, polyethyleneimine, diethanolamine, monoethanolamine, mefenamic acid, tromethamine, ethanolamine, diethanolamine, ethylenediamine, lysine, and diethylamine; and (b) at least one lipoic acid derivative represented by Formula (I):

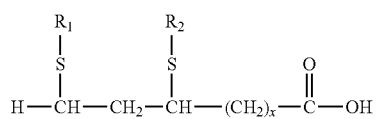
(I)

wherein $R_1$ and $R_2$ are independently selected from the group consisting of acyl defined as $R_3C(O)$—, alkyl defined as $C$—$H_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_3C(=NH)$—, hemiacetal defined as $R_4CH(OH)$—S—, and hydrogen provided that at least one of $R_1$ and $R_2$ is not hydrogen;

wherein $R_1$ and $R_2$ as defined above can be unsubstituted or substituted;

wherein $R_3$ is hydrogen, alkyl, alkenyl, alkynyl, cycloalkyl, aryl, alkylaryl, heteroaryl, or heterocyclyl, any of which can be substituted or unsubstituted;

wherein $R_4$ is $CCl_3$ or COOH; and wherein x is 0-16, n is 0-10 and m is 2-10.

In certain embodiments, the ion pairing agent is a monoalkylamine, dialkylamine, amino-substituted aliphatic alcohol, hydroxymonoalkylamine, hydroxydialkylamine, hydroxytrialkylamine, amino-substituted heteroaliphatic alcohol, alkyldiamine, substituted alkyldiamine, optionally substituted heteroaryl compound containing at least one ring nitrogen atom. In certain other embodiments, the ion pairing agent is a monoalkylamine or dialkylamine. In certain other embodiments, the ion pairing agent is amino-substituted aliphatic alcohol, hydroxymonoalkylamine, hydroxydialkylamine, hydroxytrialkylamine, or amino-substituted heteroaliphatic alcohol. In certain other embodiments, the ion pairing agent is an alkyldiamine, substituted alkyldiamine, or optionally substituted heteroaryl compound containing at least one ring nitrogen atom. In certain embodiments, the at least one ion pairing agent is triethanolamine. In certain embodiments, the at least one lipoic acid derivative is:

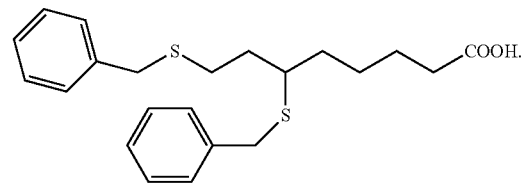 [SMILES: O=C(O)CCCCC(CCSCc1ccccc1)SCc1ccccc1]

In certain embodiments, the at least one lipoic acid derivative is bis-benzyl lipoate and the at least one ion pairing agent is triethanolamine.

II. Pharmaceutical Formulations Comprising a Lipoic Acid Derivative and Ion Pairing Agent One aspect of the present invention provides pharmaceutical formulations comprising a lipoic acid derivative and an ion pairing agent. The lipoic acid derivative and ion pairing agent form an ion pair. The pharmaceutical formulations can optionally include a pharmaceutically acceptable diluent. In particular, when a pharmaceutical formulation suitable for, e.g., intravenous administration is desired, a suitable diluent would be employed. Any conventional aqueous or polar aprotic solvent is suitable for use in the present invention. Suitable pharmaceutically acceptable diluents include, without limitation, saline, a sugar solution, alcohols such as ethyl alcohol, methanol and isopropyl alcohol, polar aprotic solvents such as dimethylformamide (DMF), dimethylsulfoxide (DMSO) and dimethylacetamide (DMA), and combinations thereof. A preferred pharmaceutically acceptable diluent is a dextrose solution, more preferably a dextrose solution containing from about 2.5% to about 10%, more preferably about 5%, dextrose by weight. The pharmaceutically acceptable diluent is typically employed in a non-homolysis generating amount; one of ordinary skill in the art can readily determine an amount of diluent suitable for use in a pharmaceutical formulation according to the present invention.

In a highly preferred embodiment of the present invention, the pharmaceutical formulation comprises bis-benzyl lipoate, triethanolamine and a dextrose solution containing about 5% dextrose by weight.

The pharmaceutical formulations of the present invention may optionally include at least one other pharmaceutically acceptable additive. Suitable additives include, without limitation, solvents, diluents, surfactants, solubilizers, preservatives, buffers, and combinations thereof, as well as any other additives particularly suited for use in parenteral administration forms. It is well within the skill of one of ordinary skill in the art to determine suitable amounts of these other pharmaceutically acceptable additives. Solvents particularly suitable for use herein include benzyl alcohol, dimethylamine, isopropyl alcohol and combinations thereof; one of ordinary skill in the art would readily recognize that it may be desirable to first dissolve the at least one lipoic acid derivative in a suitable solvent and then to dilute the solution into an ion pairing agent and finally to dilute with a diluent.

The pharmaceutical formulations of the present invention can be prepared according to conventional formulation techniques. For example, a stock solution of the at least one lipoic acid derivative and the ion pairing agent can be prepared according to conventional techniques and then diluted as desired by a pharmaceutically acceptable diluent.

The pharmaceutical formulations of the present invention are liquid preparations such as sterile parenteral solutions. The pharmaceutical formulations of the present invention may be contained in any suitable vessel such as a vial or ampoule and are suitable for administration via one of several routes including, without limitation, intravenous, intramuscular, subcutaneous, intradermally, intraperitoneal, intrathoracic, intrapleural, intrauterine or intratumor.

The pharmaceutical formulations generally described above will be more particularly described with reference to the particular embodiments below. The embodiments described below are meant to more particularly describe various aspects of the invention and should not be construed as limiting the invention.

Accordingly, one aspect of the invention provides a pharmaceutical formulation comprising:
(a) a pharmaceutically acceptable diluent; and
(b) an ion pair formed by a lipoic acid derivative and an ion pairing agent; wherein the lipoic acid derivative is a compound of Formula I represented by:

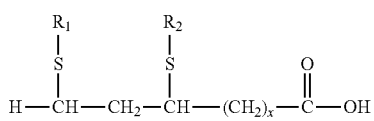
(I)

wherein $R_1$ and $R_2$ are independently selected from the group consisting of acyl defined as $R_3C(O)-$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n-S-$, imidoyl defined as $R_3C(=NH)-$, hemiacetal defined as $R_4CH(OH)-S-$, and hydrogen provided that at least one of $R_1$ and $R_2$ is not hydrogen;

wherein $R_1$ and $R_2$ as defined above can be unsubstituted or substituted;

wherein $R_3$ is hydrogen, alkyl, alkenyl, alkynyl, cycloalkyl, aryl, alkylaryl, heteroaryl, or heterocyclyl, any of which can be substituted or unsubstituted;

wherein $R_4$ is $CCl_3$ or COOH; and wherein x is 0-16, n is 0-10 and m is 2-10.

In certain embodiments, $R_1$ and $R_2$ are acetyl. In certain other embodiments, $R_1$ and $R_2$ are benzoyl. In certain other embodiments, the aryl is benzyl. In certain other embodiments, $R_1$ and $R_2$ are benzyl. In certain embodiments, the lipoic acid derivative is 6,8-bis(benzylthio)octanoic acid, which is represented by the following formula:

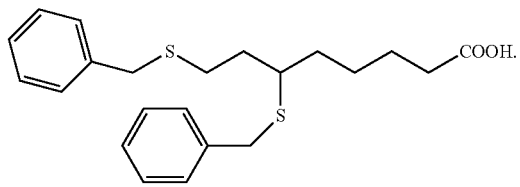 [SMILES: O=C(O)CCCCC(CCSCc1ccccc1)SCc1ccccc1]

In certain embodiments, the ion pair is present in an amount that is therapeutically effective for treating cancer in a subject. In certain embodiments, the ion pair is present in an amount that is therapeutically effective for treating a microbial infection in a subject. In certain embodiments, the ion pair is present in an amount to provide from about 0.001 $mg/m^2$ to about 10 $g/m^2$ of the lipoic acid derivative upon administration of the pharmaceutical formulation to a patient.

In certain embodiments, the ion pairing agent is an organic Bronsted base compound. In certain embodiments, the ion pairing agent is an amine compound. In certain embodiments, the ion pairing agent is a monoalkylamine, dialkylamine, trialkylamine, amino-substituted aliphatic alcohol, hydroxymonoalkylamine, hydroxydialkylamine, hydroxytrialkylamine, amino-substituted heteroaliphatic alcohol, alkyldiamine, substituted alkyldiamine, or an optionally substituted heteroaryl compound containing at least one ring nitrogen atom. In certain other embodiments, the ion pairing agent is a monoalkylamine, dialkylamine, or trialkylamine. In certain other embodiments, the ion pairing agent is amino-substituted aliphatic alcohol, hydroxymonoalkylamine, hydroxydialkylamine, hydroxytrialkylamine, or amino-substituted heteroaliphatic alcohol. In certain other embodiments, the ion pairing agent is an alkyldiamine, substituted alkyldiamine, or optionally substituted heteroaryl compound containing at least one ring nitrogen atom. In certain other embodiments, the ion pairing agent is an alkali metal hydroxide or an alkaline earth metal hydroxide. In certain other embodiments, the ion pairing agent is triethanolamine, polyethyleneimine, diethanolamine, monoethanolamine, mefenamic acid, tromethamine or a combination thereof. In certain other embodiments, the ion pairing agent is triethanolamine. In certain other embodiments, the ion pairing agent is ethanolamine, diethanolamine, ethylenediamine, lysine, diethylamine, or triethylamine. In certain other embodiments, the ion pairing agent is sodium hydroxide, potassium hydroxide, or ammonia. In certain other embodiments, the ion pairing agent is diisopropanolamine, 3-amino-1-propanol, meglumine, morpholine, pyridine, niacinamide, tris(hydroxymethyl)aminomethane, 2-((2-dimethylamino)ethoxy)ethanol, 2-(dimethylamino)ethanol, 1-(2-hydroxyethyl)pyrrolidine, triisopropanolamine, ammonium hydroxide, or cesium hydroxide. In certain other embodiments, the ion pairing agent is piperazine.

It is further contemplated that the ion pairing agent may be a polymer. In particular, a variety of polymers are contemplated for use as the ion pairing agent, including linear polymers and branched polymers. In certain embodiments, the polymer has a weight average molecular weight of about 200 g/mol to about 300,000 g/mol, about 200 g/mol to about 200,000 g/mol, about 200 g/mol to about 100,000 g/mol, about 1,000 g/mol to about 100,000 g/mol, about 5,000 g/mol to about 50,000 g/mol, or about 50,000 g/mol to about 75,000 g/mol. In certain embodiments, the polymer is a polyethylene glycol, polyethyleneimine, or dextran. In certain other embodiments, the polymer is a polyethyleneimine, dextran, or a polyethylene glycol having a weight average molecular weight of about 250 g/mol to about 100,000 g/mol. In certain embodiments, the polyethylene glycol has a weight average molecular weight of about 250 g/mol to about 40,000 g/mol, or about 500 g/mol to about 40,000 g/mol.

In certain embodiments, the ion pairing agent and lipoic acid derivative are present in a mole ratio ranging from about 1000:1 to about 1:1000. In certain other embodiments, the ion pairing agent and lipoic acid derivative are present in a mole ratio ranging from about 1:1 to about 10:1, or about 5:1 to about 10:1. In certain other embodiments, the mole ratio of the ion pairing agent and lipoic acid derivative is about 6:1, 7:1, 8:1 or 9:1. The various ion pairing agent embodiments described above are contemplated for use in forming ion pairs with all of the generic and specific lipoic acid derivatives described herein. One particularly preferred specific lipoic acid derivate is 6,8-bis(benzylthio)octanoic acid. In certain embodiments, the ion pair formed by the lipoic acid derivative and the ion pairing agent is a salt.

In certain embodiments, the diluent is selected from the group consisting of saline, a sugar solution, an alcohol, dimethylformamide, dimethylsulfoxide, dimethylacetamide and combinations thereof. In certain embodiments, the diluent is a dextrose solution. In certain other embodiments, the dextrose solution contains an amount of dextrose ranging from about 2.5% to about 10% by weight. In certain other embodiments, the pharmaceutical formulation further comprises at least one pharmaceutically acceptable additive selected from solvents, diluents, surfactants, solubilizers, preservatives, buffers, and combinations thereof.

Another aspect of the invention provides a pharmaceutical formulation comprising: bis-benzyl lipoate, and triethanolamine. In certain embodiments, the formulation further comprises a dextrose solution containing about 5% dextrose by weight.

Another aspect of the invention provides an intravenous pharmaceutical composition for treating cancer, comprising 6,8-bis(benzylthio)octanoic acid or an ion pair thereof in an amount effective for treating cancer, and a pharmaceutically acceptable aqueous diluent for solubilizing 6,8-bis(benzylthio)octanoic acid or an ion pair thereof. In certain embodiments, the diluent comprises saline. In certain embodiments, the composition provides 6,8-bis(benzylthio)octanoic acid or an ion pair thereof in an amount sufficient to provide a patient with from about 0.001 mg/m$^2$ to about 10 g/m$^2$ of 6,8-bis(benzylthio)octanoic acid per dose of the intravenous pharmaceutical composition. In certain embodiments, the composition provides 6,8-bis(benzylthio)octanoic acid or an ion pair thereof in an amount sufficient to provide a patient with from about 20 mg/m$^2$ to about 2500 mg/m$^2$ of 6,8-bis(benzylthio)octanoic acid per dose of the intravenous pharmaceutical composition. In certain embodiments, the composition provides 6,8-bis(benzylthio)octanoic acid or an ion pair thereof in an amount sufficient to provide a patient with from about 20 mg/m$^2$ to about 500 mg/m$^2$ of 6,8-bis(benzylthio)octanoic acid per dose of the intravenous pharmaceutical composition. In certain embodiments, the composition provides 6,8-bis(benzylthio)octanoic acid or an ion pair thereof in an amount sufficient to provide a patient with from about 300 mg/m$^2$ to about 700 mg/m$^2$, about 400 mg/m$^2$ to about 600 mg/m$^2$, about 380 mg/m$^2$ to about 450 mg/m$^2$, about 410 mg/m$^2$ to about 430 mg/m$^2$, about 500 mg/m$^2$ to about 700 mg/m$^2$, about 550 mg/m$^2$ to about 650 mg/m$^2$, or about 580 mg/m$^2$ to about 600 mg/m$^2$ of lipoic acid derivative, e.g., 6,8-bis(benzylthio)octanoic acid, per dose of the intravenous pharmaceutical composition. In certain embodiments, the composition comprises 6,8-bis(benzylthio)octanoic acid in the form of an ion pair. In certain other embodiments, the composition comprises 6,8-bis(benzylthio)octanoic acid in the form of an ion pair with triethanolamine.

In certain embodiments, the pharmaceutical formulations and compositions described herein contain less than 15% by weight impurities, less than 10% by weight impurities, less than 5% by weight impurities, less than 2% by weight impurities, or less than 1% by weight impurities. In a preferred embodiment, the pharmaceutical formulations and compositions described herein contain less than 2% by weight impurities.

In certain other embodiments, the lipoic acid derivative used to prepare the pharmaceutical formulations and compositions described herein has a purity of at least 35% by weight, at least 85% by weight, at least 90% by weight, at least 95% by weight, at least 98% by weight, or at least 99% by weight. In a preferred embodiment, the lipoic acid derivative used to prepare the pharmaceutical formulations and compositions described herein has a purity of at least at least 99% by weight.

In certain embodiments, the pharmaceutical formulations and compositions described herein are characterized in that exposing a population of A2780 tumor cells to the pharmaceutical formulation or composition at a concentration of a 200 μM with respect to the ion pair results in the death of greater than 70% of the tumor cells in the population (i.e., results in less than 30% tumor cell viability). Illustrative procedures for conducting an experiment to determine the degree of tumor cell death are described in Example 2 below. In certain other embodiments, the pharmaceutical formulations and compositions described herein are characterized in that exposing a population of A2780 tumor cells to the pharmaceutical formulation or composition at a concentration of a 300 μM with respect to the ion pair results in the death of greater than 95% of the tumor cells in the population (i.e., results in less than 5% tumor cell viability). In certain other embodiments, the pharmaceutical formulations and compositions described herein are characterized in that exposing a population of A2780 tumor cells to the pharmaceutical formulation at a concentration of a 400 μM with respect to the ion pair results in the death of greater than 99% of the tumor cells in the population (i.e., results in less than 1% tumor cell viability).

In certain embodiments, the pharmaceutical formulations and compositions described herein are characterized in that administering said pharmaceutical formulation or composition to a subject suffering from cancer, the pharmaceutical formulation or composition administered at an acceptably tolerated daily dosage for a period of two weeks, results in a 5% reduction in tumor volume. In certain embodiments, the pharmaceutical formulations and compositions described herein are characterized in that administering said pharmaceutical formulation or composition to a subject suffering from cancer, the pharmaceutical formulation or composition administered at an acceptably tolerated daily dosage for a period of two weeks, results in a 25%, 35%, 40%, 45%, 50%, or 60% reduction in tumor volume. In certain embodiments, the cancer is a cancer of the lung, liver, uterus, cervix, bladder, kidney, colon, breast, prostate, ovary, or pancreas. In certain embodiments, the subject suffering from cancer is a murine subject. In certain other embodiments, subject suffering from cancer is a human subject. The term "acceptably tolerated dose" is art-recognized and refers to a dose having an associated probability of toxicity as close as possible to acceptable toxicity. Acceptable toxicity means a toxicity falling within a pre-defined measure of adverse events related to the protocol treatment. See, for example, Handbook of Statistics in Clinical Oncology, 2nd ed., passim. Crowley J and Ankerst DP (eds.), 2006. New York: Chapman & Hall/CRC.)

In certain embodiments, the pharmaceutical formulations and compositions described herein are characterized in that administering said pharmaceutical formulation or composition to a subject suffering from cancer, the pharmaceutical formulation or composition administered at a therapeutically effective daily dosage for a period of two weeks, results in a 5% reduction in tumor volume. In certain embodiments, the pharmaceutical formulations and compositions described herein are characterized in that administering said pharmaceutical formulation or composition to a subject suffering from cancer, the pharmaceutical formulation or composition administered at a therapeutically effective for a period of two weeks, results in a 25%, 35%, 40%, 45%, 50%, or 60% reduction in tumor volume. In certain embodiments, the cancer is a cancer of the lung, liver, uterus, cervix, bladder, kidney, colon, breast, prostate, ovary, or pancreas. In certain embodiments, the subject suffering from cancer is a murine subject. In certain other embodiments, subject suffering from cancer is a human subject.

In certain embodiments, the pharmaceutical formulations and compositions described herein are characterized in that administering said pharmaceutical formulation or composition to a subject suffering from cancer, the pharmaceutical formulation or composition administered at an acceptably tolerated daily dosage for a period of two weeks, results in a 5% reduction in the number of cancer cells in said subject. In certain embodiments, the pharmaceutical formulations and compositions described herein are characterized in that administering said pharmaceutical formulation or composition to a subject suffering from cancer, the pharmaceutical formulation or composition administered at an acceptably tolerated daily dosage for a period of two weeks, results in a 25%, 35%, 40%, 45%, 50%, or 60% reduction in the number of cancer cells in said subject. In certain embodiments, the cancer is a cancer of the lung, liver, uterus, cervix, bladder, kidney, colon, breast, prostate, ovary, or pancreas.

In certain embodiments, the pharmaceutical formulations and compositions described herein are characterized in that administering said pharmaceutical formulation or composition to a subject suffering from cancer, the pharmaceutical formulation or composition administered at a therapeutically effective daily dosage for a period of two weeks, results in a 5% reduction in the number of cancer cells in said subject. In certain embodiments, the pharmaceutical formulations and compositions described herein are characterized in that administering said pharmaceutical formulation or composition to a subject suffering from cancer, the pharmaceutical formulation or composition administered at a therapeutically effective daily dosage for a period of two weeks, results in a 25%, 35%, 40%, 45%, 50%, or 60% reduction in the number of cancer cells in said subject. In certain embodiments, the cancer is a cancer of the lung, liver, uterus, cervix, bladder, kidney, colon, breast, prostate, ovary, or pancreas.

A number of known methods can be used to assess the volume of a tumor. Non-limiting examples of such methods include imaging methods (e.g., computed tomography (CT), magnetic resonance imaging (MRI), ultrasound, X-ray imaging, mammography, PET scans, radionuclide scans, bone scans), visual methods (e.g., colonoscopy, bronchoscopy, endoscopy), physical examination (e.g., prostate examination, breast examination, lymph nodes examination, abdominal examination, rectal examination, general palpation), blood tests (e.g., prostate specific antigen (PSA) test, carcinoembryonic antigen (CEA) test, cancer antigen (CA)-125 test, alpha-fetoprotein (AFP), liver function tests), bone marrow analyses (e.g., in cases of hematological malignancies), histopathology, cytology, and flow cytometry In yet other aspects, the invention provides a pharmaceutical formulation comprising:
(a) at least one lipoic acid derivative or salt thereof; and
(b) at least one ion pairing agent,
wherein the lipoic acid derivative and the ion pairing agent form an ion pair.

In certain embodiments, the at least one lipoic acid derivative has the formula (I):

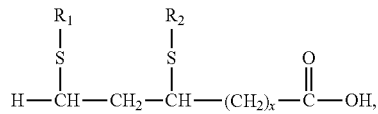

wherein $R_1$ and $R_2$ are independently selected from the group consisting of acyl defined as $R_3C(O)-$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_nS-$, imidoyl defined as $R_3C(=NH)-$, hemiacetal defined as $R_4CH(OH)-S-$, and hydrogen provided that at least one of $R_1$ and $R_2$ is not hydrogen; wherein $R_1$ and $R_2$ as defined above can be unsubstituted or substituted; wherein $R_3$ is hydrogen, alkyl, alkenyl, alkynyl, cycloalkyl, aryl, alkylaryl, heteroaryl, or heterocyclyl, any of which can be substituted or unsubstituted; wherein $R_4$ is $CCl_3$ or COOH; and wherein x is 0-16, n is 0-10 and m is 2-10. In certain embodiments, $R_1$ and $R_2$ are acetyl groups. In certain embodiments, $R_1$ and $R_2$ are benzoyl groups. In certain embodiments, the alkenyl is selected from the group consisting of propenyl, 2,3-dimethyl-2-butenyl and heptenyl. In certain embodiments, the alkynyl is selected from the group consisting of acetylenyl, propynyl and octynyl. In certain embodiments, the aryl is a benzyl or a benzyl derivative. In certain embodiments, $R_1$ and $R_2$ are each a benzyl group. In certain embodiments, the alkyl is cyclopropyl. In certain embodiments, the alkenyl is cyclopentyl. In certain embodiments, the at least one lipoic acid derivative has the formula (II):

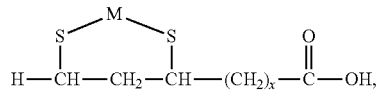

wherein M is a metal chelate, $-[C(R_1)(R_2)]_z-$ or other metal complex; wherein $R_1$ and $R_2$ are independently selected from the group consisting of acyl defined as $R_3C(O)-$, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n-S-$, imidoyl defined as $R_3C(=NH)-$, hemiacetal defined as $R_4CH(OH)-S-$, and hydrogen; wherein $R_1$ and $R_2$ as defined above can be unsubstituted or substituted; wherein $R_3$ is hydrogen, alkyl, alkenyl, alkynyl, cycloalkyl, aryl, alkylaryl, heteroaryl, or heterocyclyl, any of which can be substituted or unsubstituted; wherein $R_4$ is $CCl_3$ or COOH; and wherein x is 0-16, z is 0-5, n is 0-10 and m is 2-10.

In certain embodiments, the at least one lipoic acid derivative is present in a therapeutically effective amount. In certain embodiments, the at least one lipoic acid derivative is present in an amount to provide from about 0.001 mg/m² to about 10 g/m² of the at least one lipoic acid derivative. In certain embodiments, the at least one ion pairing agent is selected from the group consisting of triethanolamine, polyethyleneimine, diethanolamine, monoethanolamine, mefenamic acid, tromethamine and combinations thereof. In certain embodiments, the at least one ion pairing agent is triethanolamine. In certain embodiments, the at least one ion pairing agent is a polymer-conjugated ion pairing agent. In certain embodiments, the at least one ion pairing agent and the at least one lipoic acid derivative is present in a ratio ranging from about 1000:1 to about 1:1000. In certain embodiments, the pharmaceutical formulation further comprises a pharmaceutically acceptable diluent. In certain embodiments, the diluent is selected from the group consisting of saline, a sugar solution, an alcohol, dimethylformamide, dimethylsulfoxide, dimethylacetamide and combinations thereof. In certain embodiments, the diluent is a dextrose solution. In certain embodiments, the dextrose solution contains an amount of dextrose ranging from about 2.5% to about 10% by weight. In certain embodiments, the pharmaceutical formulation further comprises at least one pharmaceutically acceptable additive selected from solvents, diluents, surfactants, solubilizers, preservatives, buffers, and combinations thereof. In certain embodiments, the ion pair is a salt.

In yet other aspects, the invention provides a pharmaceutical formulation comprising bis-benzyl lipoate; and triethanolamine. In certain embodiments, the pharmaceutical formulation further comprises a dextrose solution containing about 5% dextrose by weight.

In yet other aspects, the invention provides an ion pair consisting of: at least one lipoic acid derivative; and at least one ion pairing agent. In certain embodiments, the at least one lipoic acid derivative has the formula (I):

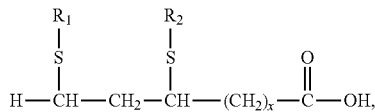

wherein $R_1$ and $R_2$ are independently selected from the group consisting of acyl defined as $R_3C(O)$—, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_3C(=NH)$—, hemiacetal defined as $R_4CH(OH)$—S—, and hydrogen provided that at least one of $R_1$ and $R_2$ is not hydrogen; wherein $R_1$ and $R_2$ as defined above can be unsubstituted or substituted; wherein $R_3$ is hydrogen, alkyl, alkenyl, alkynyl, cycloalkyl, aryl, alkylaryl, heteroaryl, or heterocyclyl, any of which can be substituted or unsubstituted; wherein $R_4$ is $CCl_3$ or COOH; and wherein x is 0-16, n is 0-10 and m is 2-10. In certain embodiments, the at least one lipoic acid derivative has the formula (II):

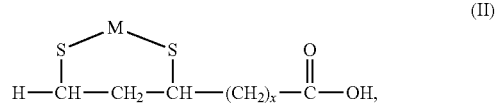

wherein M is a metal chelate, $-[C(R_1)(R_2)]_z-$ or other metal complex; wherein $R_1$ and $R_2$ are independently selected from the group consisting of acyl defined as $R_3C(O)$—, alkyl defined as $C_nH_{2n+1}$, alkenyl defined as $C_mH_{2m-1}$, alkynyl defined as $C-H_{2m-3}$, aryl, heteroaryl, alkyl sulfide defined as $CH_3(CH_2)_n$—S—, imidoyl defined as $R_3C(=NH)$—, hemiacetal defined as $R_4CH(OH)$—S—, and hydrogen; wherein $R_1$ and $R_2$ as defined above can be unsubstituted or substituted; wherein $R_3$ is hydrogen, alkyl, alkenyl, alkynyl, cycloalkyl, aryl, alkylaryl, heteroaryl, or heterocyclyl, any of which can be substituted or unsubstituted; wherein $R_4$ is $CCl_3$ or COOH; and wherein x is 0-16, z is 0-5, n is 0-10 and m is 2-10. In certain embodiments, wherein the at least one ion pairing agent is selected from the group consisting of triethanolamine, polyethyleneimine, diethanolamine, monoethanolamine, mefenamic acid, tromethamine and combinations thereof. In certain embodiments, the at least one ion pairing agent is a polymer-conjugated ion pairing agent. In certain embodiments, the at least one ion pairing agent and the at least one lipoic acid derivative is present in a ratio ranging from about 1000:1 to about 1:1000. In certain embodiments, the ion pair is a salt. In certain embodiments, the at least one lipoic acid derivative is bis-benzyl lipoate and the at least one ion pairing agent is triethanolamine.

III. Therapeutic Applications

Another aspect of the invention is directed to a method of treating a disease characterized by disease cells that are sensitive to lipoic acid derivatives comprising administering to a patient in need thereof a pharmaceutical formulation described herein. In yet other aspects, the invention provides a method of preventing a disease characterized by disease cells that are sensitive to lipoic acid derivatives comprising administering to a patient in need thereof a pharmaceutical formulation described herein.

In certain embodiments of these methods, pharmaceutical formulations of lipoic acid derivatives may be used to prevent or inhibit diseases involving altered or distinct cellular PDC activity, i.e., diseases characterized by disease cells that are sensitive to lipoic acid derivatives. Cells with appropriately altered or deranged energy metabolism, i.e., altered PDC activity, are particularly targeted and killed, while surrounding healthy tissues remain unharmed by the lipoic acid derivative. The skilled artisan can readily identify diseases having altered PDC activity. Alternatively, the skilled artisan can readily screen the disease of interest for sensitivity to lipoic acid derivatives.

In another aspect, the invention provides a method of treating or preventing a disease characterized by disease cells that are sensitive to lipoic acid derivatives, the method comprising administering to a patient in need thereof a pharmaceutical formulation described herein to treat or prevent said disease. In certain embodiments, the disease is selected from the group consisting of carcinoma, sarcoma, myeloma, lymphoma, leukemia and mixed types thereof. In certain embodiments, the disease is a microbial infection. In certain embodiments, the microbial infection is a bacterial infection, such as an infection by an *Actinomyces*, a *Campylobacter* (e.g., *Campylobacter jejuni*), an *Escherichia* (e.g., *Escherichia coli*), a *Leptospira*, a *Pseudomonas* (e.g.,

*Pseudomonas aeruginosa*), a *Shigella* (e.g., *Shigella boydii*), a *Staphylococcus* (e.g., Staphylococcal *aureus*), or a *Streptococcus* (e.g., *Streptococcus pneumoniae*) bacterium. In certain other embodiments, the microbial infection is a yeast infection (e.g., a *Candida*) or fungal infection (e.g., a *Cryptococcus*). In certain other embodiments, the microbial infection is a eukaryotic infection, e.g., by *Cryptosporidium, Giardia, Leishmania, Neospora, Plasmodia, Toxoplasma, Trichomonas*, or *Trypanosoma*.

Further aspects of the invention provide a method of treating cancer in a patient, comprising administering to a patient in need thereof a therapeutically effective amount of a pharmaceutical composition comprising 6,8-bis(benzylthio)octanoic acid or an ion pair thereof, and a pharmaceutically acceptable diluent for solubilizing 6,8-bis(benzylthio)octanoic acid or an ion pair thereof. In certain embodiments, the diluent comprises saline. In certain embodiments, the pharmaceutical composition is an intravenous pharmaceutical composition that is administered to the patient intravenously. In certain embodiments, the composition provides 6,8-bis(benzylthio)octanoic acid or an ion pair thereof in an amount sufficient to provide a patient with from about 0.001 mg/m$^2$ to about 10 g/m$^2$ of 6,8-bis(benzylthio)octanoic acid per dose of the intravenous pharmaceutical composition. In certain other embodiments, the composition provides 6,8-bis(benzylthio)octanoic acid or an ion pair thereof in an amount sufficient to provide a patient with from about 20 mg/m$^2$ to about 2500 mg/m$^2$ of 6,8-bis(benzylthio)octanoic acid per dose of the intravenous pharmaceutical composition. In certain embodiments, the composition provides 6,8-bis(benzylthio)octanoic acid or an ion pair thereof in an amount sufficient to provide a patient with from about 20 mg/m$^2$ to about 500 mg/m$^2$ of 6,8-bis(benzylthio)octanoic acid per dose of the intravenous pharmaceutical composition. In certain embodiments, the composition provides 6,8-bis(benzylthio)octanoic acid or an ion pair thereof in an amount sufficient to provide a patient with from about 300 mg/m$^2$ to about 700 mg/m$^2$, about 400 mg/m$^2$ to about 600 mg/m$^2$, about 380 mg/m$^2$ to about 450 mg/m$^2$, about 410 mg/m$^2$ to about 430 mg/m$^2$, about 500 mg/m$^2$ to about 700 mg/m$^2$, about 550 mg/m$^2$ to about 650 mg/m$^2$, or about 580 mg/m$^2$ to about 600 mg/m$^2$ of 6,8-bis(benzylthio)octanoic acid per dose of the intravenous pharmaceutical composition.

In certain embodiments, the composition comprises 6,8-bis(benzylthio)octanoic acid in the form of an ion pair. In certain other embodiments, the composition comprises 6,8-bis(benzylthio)octanoic acid in the form of an ion pair with triethanolamine.

In preferred embodiments of the methods of the present invention, the disease treated or prevented includes cancer, such as carcinoma, sarcoma, myeloma, lymphoma, leukemia and mixed types thereof. The pharmaceutical formulations of the present invention are effective against both primary and metastatic cancers and effective against cancers of the, without limitation, lung, liver, uterus, cervix, bladder, kidney, colon, breast, prostate, ovary, and pancreas. In other embodiments, the pharmaceutical formulations of the present invention can be used in the treatment of diseases associated with altered energy metabolism such as Alzheimer's disease, hyperproliferative diseases such as psoriasis and other diseases such as diabetic neuropathy.

For certain therapeutic applications, a pharmaceutical formulation is administered directly to a patient, typically in a unit dose form. In certain methods of this invention, the pharmaceutical formulation comprising the lipoic acid derivative may be administered via one of several routes including, without limitation, intravenous, intramuscular, subcutaneous, intradermally, intraperitoneal, intrathoracic, intrapleural, intrauterine or intratumor. Those skilled in the art will recognize that the mode of administering the lipoic acid derivative depends on the type of cancer or symptom to be treated. For example, a preferred mode of administering the lipoic acid for treatment of leukemia would involve intravenous administration. Likewise, those skilled in the art will also recognize that particular pharmaceutically acceptable additives will vary from pharmaceutical formulations suitable for one administration mode to pharmaceutical formulations suitable for another administration mode—the constant in all pharmaceutical formulations regardless of intended mode of administration, however, is the presence of an ion pair formed between the at least one lipoic acid derivative and the ion pairing agent.

By adapting the treatments described herein, the pharmaceutical formulations of the present invention may also be used in methods for treating diseases other than cancer, where the disease-causing cells exhibit altered metabolic patterns. For example, eukaryotic pathogens of humans and other animals are generally much more difficult to treat than bacterial pathogens because eukaryotic cells are so much more similar to animal cells than are bacterial cells. Such eukaryotic pathogens include protozoans such as those causing malaria as well as fungal and algal pathogens. Because of the remarkable lack of toxicity of the lipoic acid derivatives used in the invention to normal human and animal cells and because many eukaryotic pathogens are likely to pass through life cycle stages in which their PDCs become sensitive to lipoic acid derivatives, the pharmaceutical formulations of the present invention can be used to kill bacterial PDCs.

In general, a suitable daily dose of a ion pair compound will be that amount of the compound which is the highest tolerated dose and/or the lowest dose effective to produce a therapeutic effect. Suitable dosage formulations and methods of administering the agents are readily determined by those of skill in the art. Preferably, the ion pair compound is administered at about 0.01 mg/kg to about 200 mg/kg, more preferably at about 0.1 mg/kg to about 100 mg/kg, even more preferably at about 0.5 mg/kg to about 50 mg/kg, about 1 mg/kg to about 20 mg/kg, about 5 mg/kg to about 20 mg/kg, or about 10 mg/kg to about 30 mg/kg. In certain other embodiments, the ion pair compound is administered at about 30 mg/kg to about 125 mg/kg, at about 50 mg/kg to about 100 mg/kg, at about 60 mg/kg to about 90 mg/kg, at about 65 mg/kg to about 75 mg/kg, at about 65 mg/kg to about 85 mg/kg, or at about 60 mg/kg to about 75 mg/kg.

In certain embodiments, the methods described herein comprise administering a therapeutically effective amount of the pharmaceutical formulation to the patient at least two times per week for at least two weeks. In certain embodiments, the methods described herein comprise administering a therapeutically effective amount of the pharmaceutical formulation to the patient one to three times per week for at least two weeks. In certain embodiments, the methods described herein comprise administering a therapeutically effective amount of the pharmaceutical formulation to the patient two times per week for at least two weeks. In certain other embodiments, the methods described herein comprise administering a therapeutically effective amount of the pharmaceutical formulation to the patient one to three times per week for a period of two weeks, then no further anti-cancer therapeutics are administered to the patient for at least 3 days, at least 5 days, or at least 7 days. In certain other embodiments, the methods described herein comprise administering a therapeutically effective amount of the pharmaceutical formulation to the patient two times per week for a period of two weeks, then no further anti-cancer therapeutics are administered to the patient for at least 3 days, at least 5 days, or at least 7 days. In certain other embodiments, the methods described herein comprise administering a therapeutically effective amount of the pharmaceutical formulation to the patient two times per week for a period of two weeks, then no further anti-cancer therapeutics are administered to the patient for at least 1 week, and then the pharmaceutical formulation is administered to the patient at least two times per week for a period of at least one week. In certain other embodiments, the methods described herein comprise administering a therapeutically effective amount of the pharmaceutical formulation to the patient two times per week for a period of two weeks, then no further anti-cancer therapeutics are administered to the patient for at least 1 week, and then this dosing regimine is repeated beginning by administering a therapeutically effective amount of the pharmaceutical formulation to the patient two times per week for a period of two weeks.

Another aspect of the invention provides a method of inducing necrotic death of a cancer cell. The method comprises administering to a cancer cell an effective amount of a pharmaceutical formulation comprising (a) a pharmaceutically acceptable diluent; and (b) an ion pair formed by a lipoic acid derivative of Formula I, and an ion pairing agent that is an organic Bronsted base compound; wherein Formula I represented by:

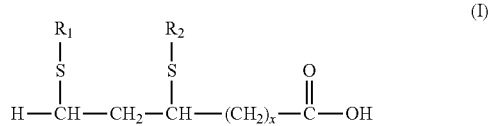

(I)

wherein $R_1$ and $R_2$ are independently selected from the group consisting of acyl defined as $R_3C(O)$—, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_3C(\!\!=\!\!NH)$—, hemiacetal defined as $R_4CH(OH)$—S—, and hydrogen provided that at least one of $R_1$ and $R_2$ is not hydrogen;

wherein $R_1$ and $R_2$ as defined above can be unsubstituted or substituted;

wherein $R_3$ is hydrogen, alkyl, alkenyl, alkynyl, cycloalkyl, aryl, alkylaryl, heteroaryl, or heterocyclyl, any of which can be substituted or unsubstituted;

wherein $R_4$ is $CCl_3$ or COOH; and wherein x is 0-16, n is 0-10 and m is 2-10.

In certain embodiments, the method preferentially induces necrotic death of the cancer cell. In particular, embodiments are contemplated where the method induces a greater proportion of cell death by necrosis, than by apoptosis. In certain embodiments, the ion pairing agent is an amine compound. In certain embodiments, the ion pairing agent is a monoalkylamine, dialkylamine, trialkylamine, amino-substituted aliphatic alcohol, hydroxymonoalkylamine, hydroxydialkylamine, hydroxytrialkylamine, amino-substituted heteroaliphatic alcohol, alkyldiamine, substituted alkyldiamine, or an optionally substituted heteroaryl compound containing at least one ring nitrogen atom. In certain other embodiments, the ion pairing agent is a monoalkylamine, dialkylamine, or trialkylamine. In certain other embodiments, the ion pairing agent is triethanolamine, polyethyleneimine, diethanolamine, monoethanolamine, mefenamic acid, tromethamine or a combination thereof. In certain other embodiments, the ion pairing agent is ethanolamine, diethanolamine, ethylenediamine, lysine, diethylamine, or triethylamine. In certain other embodiments, the ion pairing agent is diisopropanolamine, 3-amino-1-propanol, meglumine, morpholine, pyridine, niacinamide, tris(hydroxymethyl)aminomethane, 2-((2-dimethylamino)ethoxy)ethanol, 2-(dimethylamino)ethanol, 1-(2-hydroxyethyl)pyrrolidine, triisopropanolamine, or ammonium hydroxide. In certain other embodiments, the ion pairing agent is triethanolamine. In certain embodiments, the lipoic acid derivative in the pharmaceutical composition is 6,8-bis(benzylthio)octanoic acid, and said ion pairing agent is triethanolamine.

Another aspect of the invention provides a method of inducing apoptotic death of a cancer cell. The method comprises administering to a cancer cell an effective amount of a pharmaceutical formulation comprising (a) a pharmaceutically acceptable diluent; and (b) an ion pair formed by a lipoic acid derivative of Formula I, and an ion pairing agent that is an alkali metal hydroxide or an alkaline earth metal hydroxide; wherein Formula I represented by:

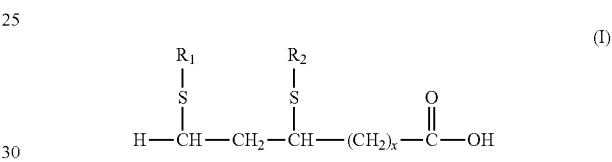

(I)

wherein $R_1$ and $R_2$ are independently selected from the group consisting of acyl defined as $R_3C(O)$—, alkyl defined as $C_nH_{2n+1}$, alkenyl defined as $C_mH_{2m-1}$, alkynyl defined as $C_mH_{2m-3}$, aryl, heteroaryl, alkyl sulfide defined as $CH_3(CH_2)_n$—S—, imidoyl defined as $R_3C(\!\!=\!\!NH)$—, hemiacetal defined as $R_4CH(OH)$—S—, and hydrogen provided that at least one of $R_1$ and $R_2$ is not hydrogen;

wherein $R_1$ and $R_2$ as defined above can be unsubstituted or substituted;

wherein $R_3$ is hydrogen, alkyl, alkenyl, alkynyl, cycloalkyl, aryl, alkylaryl, heteroaryl, or heterocyclyl, any of which can be substituted or unsubstituted;

wherein $R_4$ is $CCl_3$ or COOH; and wherein x is 0-16, n is 0-10 and m is 2-10.

In certain embodiments, the method preferentially induces apoptotic death of the cancer cell. In particular, embodiments are contemplated where the method induces a greater proportion of cell death by apoptosis, than by necrosis. In certain embodiments, the ion pairing agent is sodium hydroxide, potassium hydroxide, cesium hydroxide, calcium hydroxide, or magnesium hydroxide. In certain other embodiments, the ion pairing agent is sodium hydroxide or potassium hydroxide. In certain embodiments, the lipoic acid derivative in said pharmaceutical composition is 6,8-bis(benzylthio)octanoic acid, and said ion pairing agent is sodium hydroxide.

Specific embodiments of the invention will now be demonstrated by reference to the following examples. It should be understood that these examples are disclosed solely by way of illustrating the invention and should not be taken in any way to limit the scope of the present invention.

EXAMPLE 1

Bis-benzyl lipoate was provided in a concentrated form at a concentration of 50 mg/mL dissolved in 1M triethanolamine (TEA). The stability of the drug product was assessed by visual observation and by high-performance liquid chromatography (HPLC) assessment, performed at the beginning and the end of the study. The physical appearance did not change and the purity was found to be >99% pure, both at the beginning and the end of the study. The concentrated bis-benzyl lipoate solution was diluted to an appropriate concentration with 5% dextrose (D5W) to formulate 0.1, 1 and 10 mg/kg doses of bis-benzyl lipoate.

Comparative Example 1

Bis-benzyl lipoate was dissolved to a concentration of 40 mg/mL in a conventional mixture of Tween 80 and ethanol (1:1 by volume ratio). The concentrated bis-benzyl lipoate solution was diluted to an appropriate concentration with saline.

Testing

A study to assess the dose and dosing schedule effects on the anti-tumor activity of bis-benzyl lipoate was undertaken. More specifically, the pharmaceutical formulations of bis-benzyl lipoate of Comparative Example 1, i.e., bis-benzyl lipoate dissolved in 1:1 Tween 80:ethanol and diluted with saline, were tested in mice with Human H-460 Non Small Cell Lung Carcinoma (NSCLC) xenograft. The pharmaceutical formulations were administered intraperitoneally (IP), given 1× or 3× weekly. Administration of bis-benzyl lipoate began when the average tumor size of the mice was ~300 mm$^3$. There were originally eight treatment groups, with seven mice in each group, investigating three doses (0.1, 1 and 10 mg/kg) and two dosing schedules, as shown in Table 1 below.

TABLE 1

Original Treatment Groups.

| Treatment Group | Dose of bis-benzyl lipoate (mg/kg) | Dose Schedule | # of mice |
| --- | --- | --- | --- |
| 1 | 0 (vehicle*) | 1x weekly | 7 |
| 2 | 0 (vehicle*) | 3x weekly | 7 |
| 3 | 0.1 | 1x weekly | 7 |
| 4 | 0.1 | 3x weekly | 7 |
| 5 | 1 | 1x weekly | 7 |
| 6 | 1 | 3x weekly | 7 |
| 7 | 10 | 1x weekly | 7 |
| 8 | 10 | 3x weekly | 7 |

*vehicle refers to a Tween 80/ethanol/saline mixture

The results (as shown in FIGS. 1A and 1B) showed that bis-benzyl lipoate did not induce any anti-tumor effects, when compared to vehicle treatment.

Next, the protocol was revised by subdividing each treatment group into two subgroups, as shown in Table 2 below. Specifically, both subgroups of each treatment group were treated with the same dose of bis-benzyl lipoate as in the original protocol; however, one of the two subgroups was treated with a pharmaceutical formulation of bis-benzyl lipoate according to Comparative Example 1, i.e., bis-benzyl lipoate dissolved in 1:1 Tween 80:ethanol and diluted with saline, and the other subgroup was treated with a pharmaceutical formulation of bis-benzyl lipoate according to Example 1, i.e., dissolved in TEA and diluted with D5W.

TABLE 2

Revised Treatment Groups.

| Group | | Bis-benzyl lipoate (mg/kg) | Dose Schedule | Vehicle | #mice |
| --- | --- | --- | --- | --- | --- |
| 1 | A | 0.1 | 1x weekly | TEA | 4 |
| & | B | 1 | 1x weekly | TEA | 3 |
| 2 | A | 10 | 1x weekly | TEA | 4 |
| | B | 10 | 1x weekly | Tween 80:Ethanol | 3 |
| 3 | A | 0.1 | 1x weekly | Tween 80:Ethanol | 4 |
| | B | 0.1 | 1x weekly | TEA | 3 |
| 4 | A | 0.1 | 3x weekly | Tween 80:Ethanol | 4 |
| | B | 0.1 | 3x weekly | TEA | 3 |
| 5 | A | 1 | 1x weekly | Tween 80:Ethanol | 3 |
| | B | 1 | 1x weekly | TEA | 4 |
| 6 | A | 1 | 3x weekly | Tween 80:Ethanol | 3 |
| | B | 1 | 3x weekly | TEA | 4 |
| 7 | A | 10 | 1x weekly | Tween 80:Ethanol | 4 |
| | B | 10 | 1x weekly | TEA | 3 |
| 8 | A | 10 | 3x weekly | Tween 80:Ethanol | 4 |
| | B | 10 | 3x weekly | TEA | 3 |

The results showed that H-460 tumors in mice treated with 0.1-10 mg/kg of bis-benzyl lipoate in pharmaceutical formulations made according to Example 1 may be similar among each other, but may be smaller than that in mice treated with 10 mg/kg of bis-benzyl lipoate in a pharmaceutical formulation made according to Comparative Example 1.

Next, again the protocol was revised to change the pharmaceutical formulation tested for anti-tumor efficacy to exclusively pharmaceutical formulations made according to Example 1, i.e., dissolved in TEA and diluted with D5W. There were ten treatment groups, with 8 mice in each group, investigating three doses (0.1, 1 and 10 mg/kg) and three dosing schedules, as shown in Table 3 below.

TABLE 3

Second Revised Treatment Groups.

| Treatment Group | Dose of bis-benzyl lipoate (mg/kg) | Dose Schedule | # of mice |
| --- | --- | --- | --- |
| 1 | 0 (vehicle*) | 5x weekly | 8 |
| 2 | 0.1 | 1x weekly | 8 |
| 3 | 0.1 | 3x weekly | 8 |
| 4 | 0.1 | 5x weekly | 8 |
| 5 | 1 | 1x weekly | 8 |
| 6 | 1 | 3x weekly | 8 |
| 7 | 1 | 5x weekly | 8 |
| 8 | 10 | 1x weekly | 8 |
| 9 | 10 | 3x weekly | 8 |
| 10 | 10 | 5x weekly | 8 |

*vehicle refers to D5W only

The results (as shown in FIGS. 2A-2C) showed that bis-benzyl lipoate in pharmaceutical formulations prepared according to Example 1 (TEA/D5W) at 0.1, 1 and 10 mg/kg, given 1×, 3× or 5× weekly induced a similar and significant degree of tumor growth inhibition as compared with the results obtained when pharmaceutical formulations prepared according to Comparative Example 1 (Tween 80/ethanol/saline) were similarly tested.

EXAMPLE 2

Numerous formulations of CPI-613 were tested for their ability to kill A2780 ovarian tumor cells and BXPC3 human pancreatic cancer cells using an in vitro assay. The effect of the formulation vehicle alone on A2780 ovarian tumor cells and BXPC3 human pancreatic cancer cells was also evaluated. The experimental procedures and results are described below.

Experimental Procedures:

1. Materials and Human Tumor Cells

Materials for the experiments were obtained through normal distribution channels from commercial vendors. For example, Costar opaque-walled plates were obtained from Corning Costar Corporation of Cambridge, Mass. (cat. no. 3917). FLUOstar OPTIMA was obtained from BMG LABTECH of Offenburg, Germany. CellTiter Glo® Luminescent Cell Viability Assay materials were obtained from Promega (Fisher Scientific cat no. PR-G7573). RPMI 1640 Tissue culture medium was obtained from Mediatech (Fisher Scientific cat. no. MT-10040-CV). The Fetal Bovine Serum (FBS) corresponded to Fisher Scientific cat. no. MTT35011CV, and the penicillin and steptomycin correspond to Fisher Scientific cat. no. MT 30-009-CI Two types of human tumor cells were used in this investigation: BXPC3 human pancreatic cancer cells and A2780 human ovarian cancer cells. The BXPC3 cells were originally obtained from American Type Cell Culture (ATCC). The ovarian tumor cells were gifts from Roswell Park Cancer Institute, Buffalo, N.Y. All tumor cells were maintained at 37° C. in a humidified 5% $CO_2$ atmosphere in T75 tissue culture flasks containing 20 mL of Roswell Park Memorial Institute (RPMI) 1640 containing 2 mM L-glutamine, 10% fetal bovine serum (FBS) and 1% penicillin and streptomycin (100 IU/mL penicillin and 100 µg/mL streptomycin). The tumor cells were split at a ratio of 1:5 every 4-5 days by trypsinization and resuspended in fresh medium in a new flask. Cells were harvested for experiments at 70-90% confluency.

2. Preparation of CPI-613 Formulations in Different Vehicles for Cell Viability Assays CPI-613 (i.e., 6,8-bis(benzylthio)octanoic acid) stock solutions at concentrations of 8, 4, 2, 1.5 and 0.5 mM were prepared in the appropriate vehicles. The molar ratio of vehicle to CPI-613 was maintained at 8:1. The corresponding vehicle concentrations were 64, 32, 16, 12, and 4 mM respectively. A sixty-four mM aliquot of vehicle was dissolved in 10 mL of water. Next, 8 mM of CPI-613 was added and the mixture was stirred until a clear solution was obtained. The resulting 8 mM drug/64 mM vehicle formulation was then serially diluted with water to give a 4 mM drug/32 mM vehicle and 2 mM drug/16 mM vehicle solution. The appropriate amount of water was added to the 2 mM drug/16 mM vehicle solution to give 1.5 mM drug/12 mM vehicle and 0.5 mM drug/4 mM vehicle solutions. A 5 µL aliquot of this stock solution was added to 95 µL of tumor cells in media. Upon dilution in the wells, the corresponding drug concentrations were 400, 200, 100, 75 and 25 µM respectively.

3. Preparation of CPI-613 Alkali Salts and CPI-613 Ammonium Salt for Cell Viability Assays For the sodium salt and potassium salt form of CPI-613, 1 equivalent of CPI-613 solid was dissolved in water. Sixty-two mg of CPI-613 (0.00016 mol) was added to 10 mL of water, then 165 µL of 1M NaOH or KOH was added and stirred until a clear solution was obtained. This gave a 16 mM solution. The resulting 16 mM solution was then serially diluted, thereby providing 8 mM and 4 mM solutions of the CPI-613 salt form. For the ammonium salt, vehicle to drug ratio was maintained at 8:1 and the formulation was prepared using procedures analogous to those described above in Section 2 relating to preparation of CPI-613 formulations in different vehicles.

4. Preparation of CPI-613 Formulations for in Different Vehicles for Cell Viability Assays CPI-613 formulated in 1M triethanolamine (TEA) was used as an internal control during formulation screening. To prepare a 16 mM of working stock of CPI-613, 50 mg/mL of CPI-613 (128.66 mM of CPI-613 in 1M TEA) was diluted in complete cell culture media containing 10% FBS. That is, 310 µL of a 128.66 mM solution of CPI-613 in 1M TEA was added to 2.19 mL of cell culture media. This stock was further diluted serially in complete media to give 8 mM, 4 mM 2 mM, 1.5 mM and 0.5 mM working solutions. On the day of testing, 5 µL of this working solution was added to 95 µL of cell culture media (20 fold dilution) resulting final concentrations of 400, 200, 100, 75 and 25 µM CPI-613, respectively. The ratio of CPI-613 to TEA was maintained at 1:8 ratio at all times.

5. Study Design

The cell viability of CPI-613 formulations formulated at a ratio of 1:8, CPI-613 to vehicle, was assessed by exposing the A2780 ovarian tumor cells and BXPC3 human pancreatic cancer cells to the following CPI-613 concentrations: 400 µM (3200 µM vehicle), 200 µM (1600 µM vehicle), 100 µM (800 µM vehicle), 75 µM (600 µM vehicle) and 25 µM (200 µM vehicle) The impact of corresponding vehicles at 3200, 1600 and 800 µM concentrations was also tested in tumor cells for cell viability. Tumor cells were also treated with 25 µM, 75 µM, 100 µM, 200 µM and 400 µM of salt analogs of CPI-613. CPI-613 in TEA was used as an internal control. The tumor cells were treated for 24 hrs with the test article in serum-containing medium. After 24 hrs of treatment the number of viable tumor cells was determined.

6. Study Procedures

Part I: Cell Seeding for Experiments

Cells were grown to 70-90% confluency, medium was removed and the cell monolayers were washed briefly by adding 5 mL of phosphate buffer saline (PBS) followed by aspiration. Trypsin-ethylenediaminetetraacetic acid (EDTA) (4 mL) was added to each flask, and the flask was placed in the tissue culture incubator for 5 minutes. Serum-containing medium (10 mL) was added to halt the enzymatic reactions, and cells were disaggregated by repeated resuspension with serological pipette. The cell-containing medium (20 µL) was added to 20 µL of 0.4% Trypan Blue solution, mixed, and 10 µL of this cell-containing mixture was placed in a chamber of the hemocytometer. The number of viable cells were determined by counting the number of viable cells (cells that excluded Trypan blue) in the 4 corner squares of the hemocytometer chamber at 100× magnification, to get the average number of cells present. The volume of cells needed was determined by the following formula:

$$\text{Volume of cells needed} = \frac{\text{\# of cells need for the assay (mL)}}{\text{\# of cells counted (mL)}}$$

where: # of cells counted (mL)=average # of cells on hemocytometer×2 (dilution factor)×$10^4$.

The number of cells targeted for the study was 4×$10^3$ per well in 100 µL of medium. The actual number of cells were counted and seeded in the wells of a 96 well-plate. The cells were incubated for ~24 hrs before addition of CPI-613.

Part II: Treatment with Test Article

For each cell line the concentrations of test articles or vehicles specified above was used. Five µL of the working solution for each test article or vehicle was added to 95 µL of cell culture media. The corresponding final concentrations of test articles are 20 fold more diluted than the working solutions. After exposure to the test articles for 24 hrs, the number of viable cells in each well was determined and the percent of viable cells relative to control (in the absence of CPI-613) were calculated. Additionally, a set of wells was treated with cell culture medium in the absence of cells to obtain a value for background luminescence. A separate set of cells was seeded at the same time in a clear 96 well plate and observed under the microscope at 24 hrs, following addition of CPI-613 to estimate the amount of cells present after treatment.

Part III: Determination of the Number of Viable Cells by the CellTiter Glo® Assay The number of viable cells was determined by using the CellTiter Glo® Assay. Specifically, reagents were mixed and allowed to come to room temperature according to instructions from Promega, Inc. (Madison, Wis.). Cell plates were removed from the cell culture incubator and left on the bench for 30 minutes until they reach room temperature. A one-hundred μL aliquot CellTiter Glo® reagent was added to each well with a 12-channel Eppendorf pipettor. The cells were lysed by shaking the plate for 2 minutes in a shaker. Then, the cells were kept at room temperature for 10 minutes to stabilize the luminescent signal. The luminescence was measured using the FLUOstar OPTIMA plate reader (BMG Labtech, Inc., Durham, N.C.).

Part IV: Calculations of $EC_{50}$ Values

Data from luminescence readings was copied onto EXCEL spreadsheets, and cell growth relative to untreated cells was calculated, using the following equation:

$$\% \text{ growth related to } NT = \frac{\text{mean luminescence of the test article}}{\text{mean luminescence untreated}} \times 100\%$$

The calculated values were imported into SigmaPlot, v11. A Four-Parameter Logistic Curve of the "mean relative cell growth as a function of the concentrations of the test articles" was generated. The $EC_{50}$ values were determined from the curves. The R-squared value provides an indication of the degree of fitness of data to the curve. For each experiment, the percentage of viable cells was be expressed as the mean of 9 replicates. The average was calculated by taking the mean±standard deviation of the three experiments.

Results:

Results from the above-described experiment are presented below in sections according to the nature of the experiment.

Part I: Impact of Formulation Vehicles on Tumor Cell Viability

The vehicles used in CPI-613 formulations were assessed for their impact on tumor cell viability at a concentration of 3200, 1600 and 800 μM. The results from these assays are shown in Tables 4 and 5 below. The data indicate that at vehicle concentrations of 800 μM and 1600 μM all the vehicles tested did not have a significant effect on tumor cell kill in both A2780 & BXPC3 cell lines. At a vehicle concentration of 3200 μM, the following vehicles appear to have come cell killing effects: triisopropanolamine, ethylenediamine, and diisopropanolamine. The vehicles diethanolamine, meglumine, 3-amino-1-proponol, triethylamine, aminopropanediol, tris base, lysine, diethylamine and piperazine did not show a significant impact on cancer cell killing at a concentration of 3200 μM, and it is contemplated that these vehicles can be used to formulate CPI-613 even at very high concentrations of the vehicle.

In particular, Table 4 shows the impact of formulation vehicles on A2780 tumor cell viability. Table 5 shows the impact of formulation vehicles on BXPC3 tumor cell viability. The results are the average of three experiments with each experiment having 4 replicates. The symbol + indicates a tumor cell viability of >95%, the symbol ++ indicates a tumor cell viability of >85% up to 95%, the symbol +++ indicates a tumor cell viability of >70% up to 85%, the symbol ++++ indicates a tumor cell viability of <70%. Tumor cell viability refers to the percentage of tumor cells in the population that remain alive following treatment with the test substance. For example, a tumor cell viability of >95% means that greater than 95% of the cells in the population are alive following treatment with the test substance. A tumor cell viability of <70% percent means that less than 70% of the cells in the population are alive following treatment with the test substance.

TABLE 4

A2780 Tumor Cell Viability in the Presence of Various Formulation Vehicles.

| Vehicle | A2780 Cell Viability | | |
|---|---|---|---|
| Concentration | 800 μM | 1600 μM | 3200 μM |
| Non Treated | + | + | + |
| Ethanolamine | + | + | + |
| Diethanolamine | ++ | ++ | + |
| Meglumine | + | + | + |
| 3-amino-1-proponol | + | + | ++ |
| Triisopropanolamine | + | + | +++ |
| Triethylamine | + | + | + |
| Aminopropanediol | + | + | + |
| Tris base | + | + | + |
| Ethylenediamine | ++ | ++ | ++++ |
| Lysine | + | + | + |
| Diisopropanolamine | + | + | ++++ |
| Diethylamine | + | + | ++ |
| Piperazine | ++ | +++ | ++ |

TABLE 5

BXPC3 Tumor Cell Viability in the Presence of Various Formulation Vehicles.

| Vehicle | BXPC3 Cell Viability | | |
|---|---|---|---|
| Concentration | 800 μM | 1600 μM | 3200 μM |
| Non Treated | + | + | + |
| Ethanolamine | ++ | ++ | ++ |
| Diethanolamine | ++ | ++ | ++ |
| Meglumine | ++ | ++ | ++ |
| 3-amino-1-proponol | + | ++ | ++ |
| Triisopropanolamine | + | + | +++ |
| Triethylamine | + | + | + |
| Aminopropanediol | + | + | + |
| Tris base | + | + | + |
| Ethylenediamine | + | +++ | ++++ |
| Lysine | + | + | + |
| Diisopropanolamine | + | + | +++ |
| Diethylamine | + | +++ | ++++ |
| Piperazine | ++ | ++ | +++ |

Part II: Impact of CPI-613 Formulations on Cell Viability

The effect of different CPI-613 formulations prepared using clinically approved vehicles was tested. The ratio of CPI-613 to vehicle was maintained at a 1:8 ratio. The cell viability of tumor cells, that were exposed to different CPI-613 concentrations ranging from 25-400 μM were measured using CellTiter Glo® Assay. The results of this experiment are summarized in Tables 6-7 and FIGS. 3-11. In particular, the data in Tables 6-7 are the average of 2-3 experiments each having 4 replicates each. The percent cell viability was determined compared to non-treated control, and the ratio of CPI-613 to vehicle was maintained at 1:8 in these experiments. It is noted, however, that although a 1:8 ratio of CPI-613 to vehicle was used in these formulations, it is contemplated that formulations having a lower ratio of CPI-613 to vehicle may be amenable in certain instances.

In Tables 6-7, the symbol + indicates a tumor cell viability of >95%, the symbol ++ indicates a tumor cell viability of >70% up to 95%, the symbol +++ indicates a tumor cell viability of >30% up to 70%, the symbol ++++ indicates a tumor cell viability of >10% up to 30%, and the symbol +++++ indicates a tumor cell viability of <10%.

TABLE 6

Impact of CPI-613 Formulations on A2780 Cell Viability.

| | A2780 Cell Viability at Certain Concentrations of CPI-613 & Vehicle CPI-613 Concentration (µM) | | | | | |
|---|---|---|---|---|---|---|
| | 0 | 25 | 75 | 100 | 200 | 400 |
| | Vehicle Concentration (µM) | | | | | |
| | 800 | 200 | 600 | 800 | 1600 | 3200 |
| Not Treated | + | + | + | + | + | + |
| CPI-613 in triethanolamine | + | + | + | ++ | ++++ | +++++ |
| CPI-613 in ethanolamine | + | + | ++ | ++ | +++ | +++++ |
| CPI-613 in diethanolamine | + | + | ++ | ++ | ++++ | +++++ |
| CPI-613 in meglumine | + | + | ++ | ++ | ++++ | +++++ |
| CPI-613 in 3-amino-1-proponol | + | + | ++ | ++ | ++++ | +++++ |
| CPI-613 in triethylamine | + | ++ | ++ | ++ | +++ | +++++ |
| CPI-613 in ethylenediamine | ++ | + | ++ | +++ | ++++ | +++++ |
| CPI-613 in lysine | + | + | ++ | ++ | +++ | +++++ |
| CPI-613 in diisopropanolamine | + | + | ++ | ++ | ++++ | +++++ |
| CPI-613 in diethylamine | + | ++ | ++ | ++ | +++ | +++++ |

TABLE 7

Impact of CPI-613 Formulations on BXPC3 Cell Viability.

| | BXPC3 Cell Viability at Certain Concentrations of CPI-613 & Vehicle CPI-613 Concentration (µM) | | | | | |
|---|---|---|---|---|---|---|
| | 0 | 25 | 75 | 100 | 200 | 400 |
| | Vehicle Concentration (µM) | | | | | |
| | 800 | 200 | 600 | 800 | 1600 | 3200 |
| Not Treated | + | + | + | + | + | + |
| CPI-613 in triethanolamine | + | + | ++ | ++ | ++++ | +++++ |
| CPI-613 in ethanolamine | + | + | + | ++ | +++ | +++++ |
| CPI-613 in diethanolamine | + | + | + | ++ | +++ | +++++ |
| CPI-613 in meglumine | + | + | ++ | ++ | +++ | +++++ |
| CPI-613 in 3-amino-1-proponol | + | + | ++ | ++ | +++ | +++++ |
| CPI-613 in triethylamine | + | + | ++ | ++ | +++ | +++++ |
| CPI-613 in ethylenediamine | ++ | + | ++ | ++ | +++ | +++++ |
| CPI-613 in lysine | + | + | + | ++ | +++ | +++++ |
| CPI-613 in diisopropanolamine | + | + | + | ++ | +++ | +++++ |
| CPI-613 in diethylamine | + | + | ++ | ++ | +++ | +++++ |

Results from the experiment indicate, for example, that exposure of the test cancer cells to the CPI-613 in triethanolamine formulation at a concentration of 100 µM resulted in the death of approximately 20% of the cancer cells in the population. Exposure of the test cancer cells to the CPI-613 in triethanolamine formulation at a concentration of 200 µM resulted in the death of approximately 70-80% of the cancer cells in the population, and exposure of the test cancer cells to the CPI-613 in triethanolamine formulation at a concentration of 400 µM resulted in the death of approximately 100% of the cancer cells in the population. CPI-613 in any one of ethanolamine, diethanolamine, meglumine, 3-amino-1-proponol, triethylamine, ethylenediamine, lysine, diisopropanolamine and diethylamine at a concentration of 200 µM concentration resulted in the death of more than 50% of the cancer cells, and, at a concentration of 400 µM all of the formulations caused death of 100% of the cancer cells based on detection methods.

Figure 12:
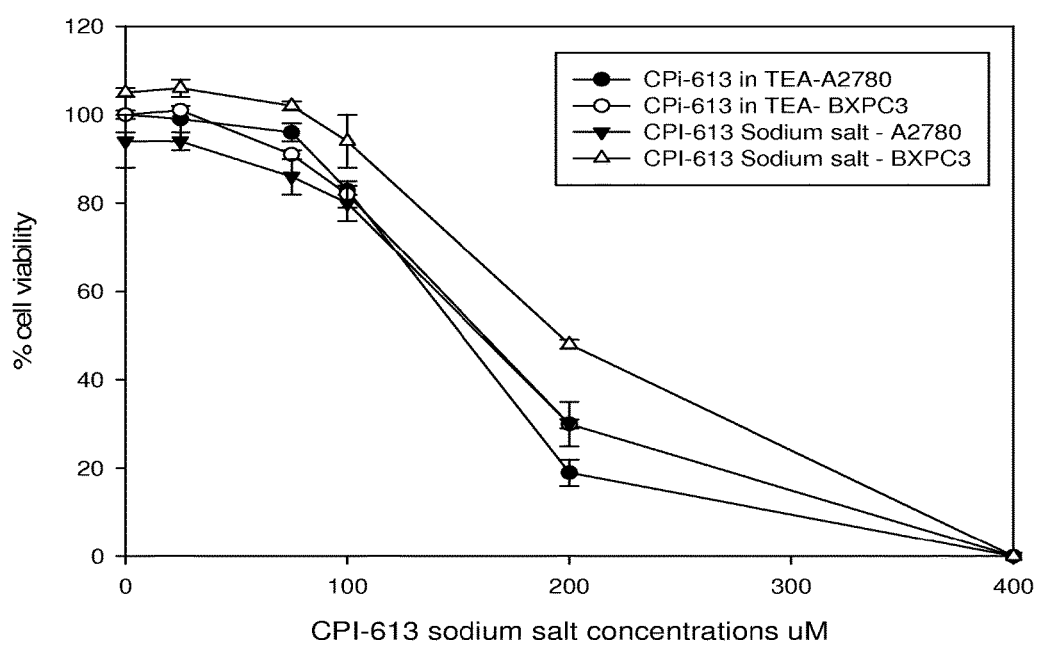
FIG. 12 shows percent viability of A2780 and BXPC3 tumor cells treated with either CPI-613 in triethanolamine or CPI-613 sodium salt.
Figure 13:
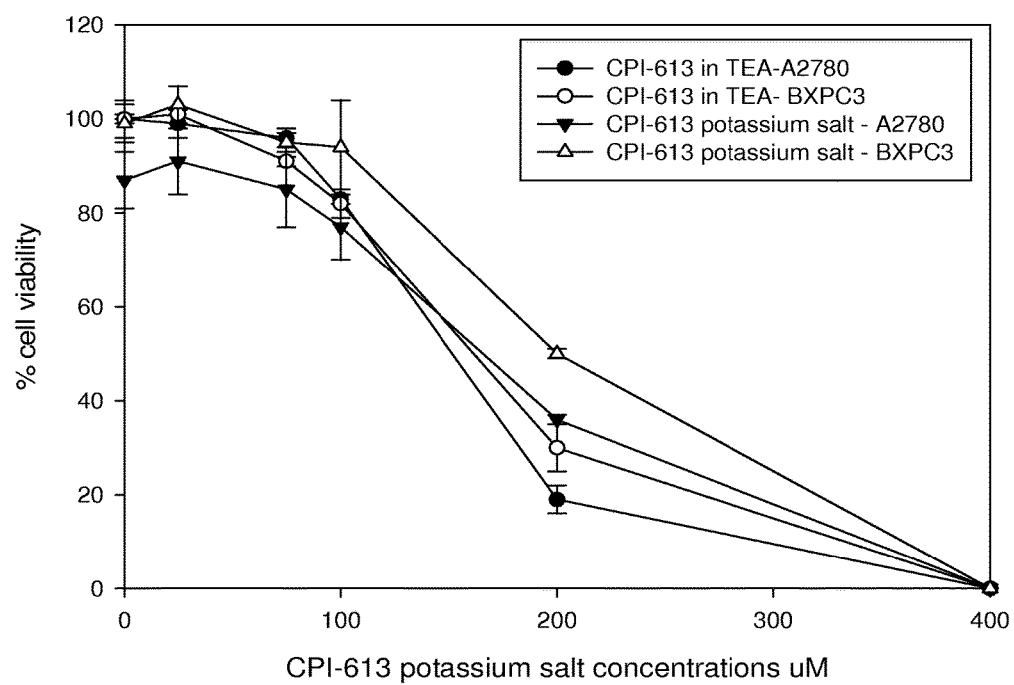
FIG. 13 shows percent viability of A2780 and BXPC3 tumor cells treated with either CPI-613 in triethanolamine or CPI-613 potassium salt.
Figure 14:
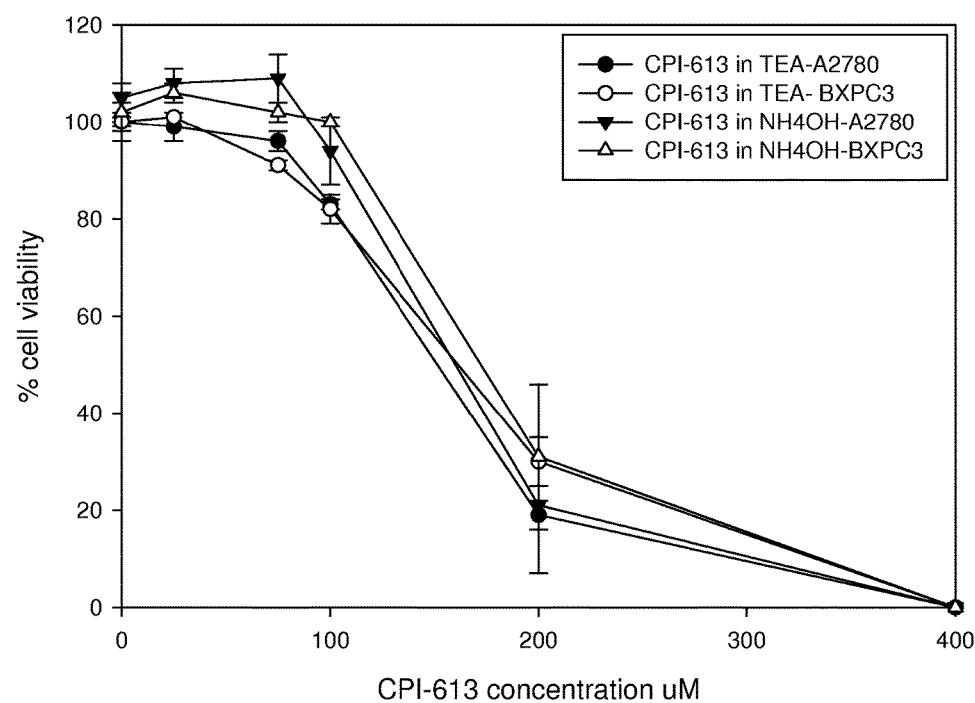
FIG. 14 shows percent viability of A2780 and BXPC3 tumor cells treated with either CPI-613 in triethanolamine or CPI-613 in ammonium hydroxide.

Part III: Impact of CPI-613 Alkali Salts and CPI-613 Ammonium Salt Formulations on Cell Viability The effect of different CPI-613 salt formulations described above were tested. The viability of tumor cells exposed to CPI-613 salt formulations was measured using a CellTiter Glo® Assay. Experiments were conducted measuring cell viability when the tumor cells were exposed to CPI-613 salt formulations ranging in concentration from 25-400 µM. Moreover, the ratio of CPI-613 to base was maintained at 1:1 in the sodium salt and the potassium salt formulation, whereas in the ammonium salt formulation the ratio was 1:8. The results are shown in Tables 8-11 and FIGS. 12-14 and are an average of three experiments each having four replicates. The percent cell viability was determined compared to a control experiment where the cells were not treated with CPI-613 salt formulation. In Tables 8-11, the symbol + indicates a tumor cell viability of >95%, the symbol ++ indicates a tumor cell viability of >70% up to 95%, the symbol +++ indicates a tumor cell viability of >30% up to 70%, the symbol ++++ indicates a tumor cell viability of >10% up to 30%, and the symbol +++++ indicates a tumor cell viability of <10%.

TABLE 8

Impact of CPI-613 Alkali Salt Formulations on Viability of A2780 Cells.

| CPI-613 | A2780 Cell Viability at Certain Concentrations | | | | | |
|---|---|---|---|---|---|---|
| Concentration (μM) | 0 | 25 | 75 | 100 | 200 | 400 |
| Not treated | + | + | + | + | + | + |
| CPI-613 sodium salt | ++ | ++ | ++ | ++ | ++++ | +++++ |
| CPI-613 potassium salt | ++ | ++ | ++ | ++ | +++ | +++++ |

TABLE 9

Impact of CPI-613 Alkali Salt Formulations on Viability of BXPC3 Cells.

| CPI-613 | BXPC3 Cell Viability at Certain Concentrations | | | | | |
|---|---|---|---|---|---|---|
| Concentration (μM) | 0 | 25 | 75 | 100 | 200 | 400 |
| Not treated | + | + | + | + | + | + |
| CPI-613 sodium salt | + | + | + | ++ | +++ | +++++ |
| CPI-613 potassium salt | + | + | ++ | ++ | +++ | +++++ |

TABLE 10

Impact of CPI-613 Ammonium Salt Formulations on Viability of A2780 Cells.

| CPI-613 | A2780 Cell Viability at Certain Concentrations | | | | | |
|---|---|---|---|---|---|---|
| Concentration (μM) | 0 | 25 | 75 | 100 | 200 | 400 |
| Not treated | + | + | + | + | + | + |
| CPI-613 in triethanolamine (control) | + | + | + | ++ | ++++ | +++++ |
| CPI-613 ammonium salt | + | + | + | ++ | ++++ | +++++ |

TABLE 11

Impact of CPI-613 Ammonium Salt Formulations on Viability of BXPC3 Cells.

| CPI-613 | BXPC3 Cell Viability at Certain Concentrations | | | | | |
|---|---|---|---|---|---|---|
| Concentration (μM) | 0 | 25 | 75 | 100 | 200 | 400 |
| Not treated | + | + | + | + | + | + |
| CPI-613 in triethanolamine (control) | + | + | ++ | ++ | ++++ | +++++ |
| CPI-613 ammonium salt | + | + | + | + | +++ | +++++ |

Results from the experiment indicate, for example, that the CPI-613 sodium salt and CPI-613 potassium salt formulation provided almost 65% cell kill (i.e., death of almost 65% of the cancer cells in the population) in A2780 cells and almost 50% cell kill in BXPC3 cells when the cells where exposed to these CPI-613 salt formulations at 200 μM. Further, when the A2780 cells and BXPC3 cells were exposed to these CPI-613 salt formulations at a concentration of 400 μM, all the cells were killed for both cell lines. The CPI-613 ammonium salt formulation provided approximately 70-80% cell kill when the cells were exposed to the formulation at concentration 200 μM, and 100% cell kill was observed following administration of the CPI-613 ammonium salt formulation at a concentration of 400 μM.

EXAMPLE 3

In this example, the type of cell death that occurs following administration of CPI-613 triethanolamine and CPI-613 sodium salt was evaluated. The experimental procedures and results are described below.

Experimental Procedures:

Part I—Equipment

Subsequent to propidium iodide (PI)/Annexin Alexa Fluor 488 staining, necrotic and apoptotic BXPC3 cells were assessed with the aid of Fluorescence Activated Cell Sorting (FACS) Scan Flow Cytometer (FACS Calibur Instrument, BD Biosciences, San Jose, Calif.) and CellQuest software (BD Biosciences, San Jose, Calif.). This software identifies the quantity of DNA content. Apoptotic cells will stain Annexin V positive but PI negative because the PI cannot cross the intact cell membrane. Necrotic cells will stain positive for both Annexin V and PI because the cell membrane is not intact.

Part II—Materials

The reagent used for PI/Annexin Alexa Fluor 488 Staining of BXPC3 Cells was supplied by the Invitrogen/Molecular Probes Vybrant Apoptosis Assay Kit #2 cat # V13241.

Part III—Human Cancer Cells:

BxPC3 human pancreatic cancer cells were used in this investigation. These tumor cells were originally obtained from American Type Cell Culture (ATCC, Manassas, Va.). These cells had been tested negative for viral contamination using the Mouse Antibody Production (MAP) test, performed by Charles River Labs Molecular Division, upon the receipt of the tumor cells from ATCC. The tumor cells were maintained at 37° C. in a humidified 5% $CO_2$ atmosphere in T225 tissue culture flasks containing 50 mL of Roswell Park Memorial Institute (RPMI)-1640 solution with 10% Fetal Bovine Serum (FBS) and 2 mM L-glutamine. Cells were split at a ratio of 1:10 every 2-3 days by trypsinization and resuspended in fresh medium in a new flask. Cells were harvested for experiments in the same way at 70-90% confluency.

Part IV—Plating of BxPC3 Cells

BxPC3 cells were plated at a density of $0.3 \times 10^6$ cells per well in a sterile 6-well tissue culture plate (Falcon multiwell plate cat #353046) 48 hours prior to drug treatment.

Part IV—Treatment Groups

The following treatment groups were utilized in this experiment: 1) Non-treated BxPC3 cells not drug (control), 2) Triethanolamine (TEA) with no drug as a stock solution of 700 mM with final concentration on the cells being 2.1 mM, 3) CPI-613 in TEA as a stock solution of 100 mM of CPI-613 in 700 mM TEA with final concentration on the cells being 300 μM of CPI-613 in 2.1 mM TEA, 4) Sodium salt of CPI-613 as a stock solution of 100 mM with final concentration on the cells being 300 μM, and 5) 0.9% NaCl with no CPI-613.

Part V—Design of Experiment:

The experiment was conducted in accordance with the steps identified below:

1) BxPC3 cells were plated at a density of $0.3 \times 10^6$ cells per well in a sterile 6-well tissue culture plate (Falcon multiwell plate cat #353046) 48 hours prior to drug treatment.

2) A 1 mL aliquot of each test condition was added to corresponding well. Each treatment condition was run in duplicate. Cells were incubated for 24 hours with test conditions prior to PI/Annexin Staining.

3) After 24 hours, cells, including floating cells, with media were harvested and centrifuged at 1,400 RPM for 5 minutes.

4) For all samples the supernatant was aspirated off, and the pellet was resuspended in 3 mL PBS and then centrifuged again at 1,400 RPM for 5 minutes, for a total of 2 washes.

5) After the last wash, each pellet was then resuspended with 200 µL 1× Annexin V binding buffer, 1 µL PI, and 3 µL Annexin Alexa Fluor 488. Cells were incubated with PI/Annexin V for 8 minutes.

6) The reaction was stopped by adding 400 µL 1× Annexin V binding buffer.

7) Samples were then taken to FACS facility to be read on the FACS Scan Flow Cytometer.

Figure 15:
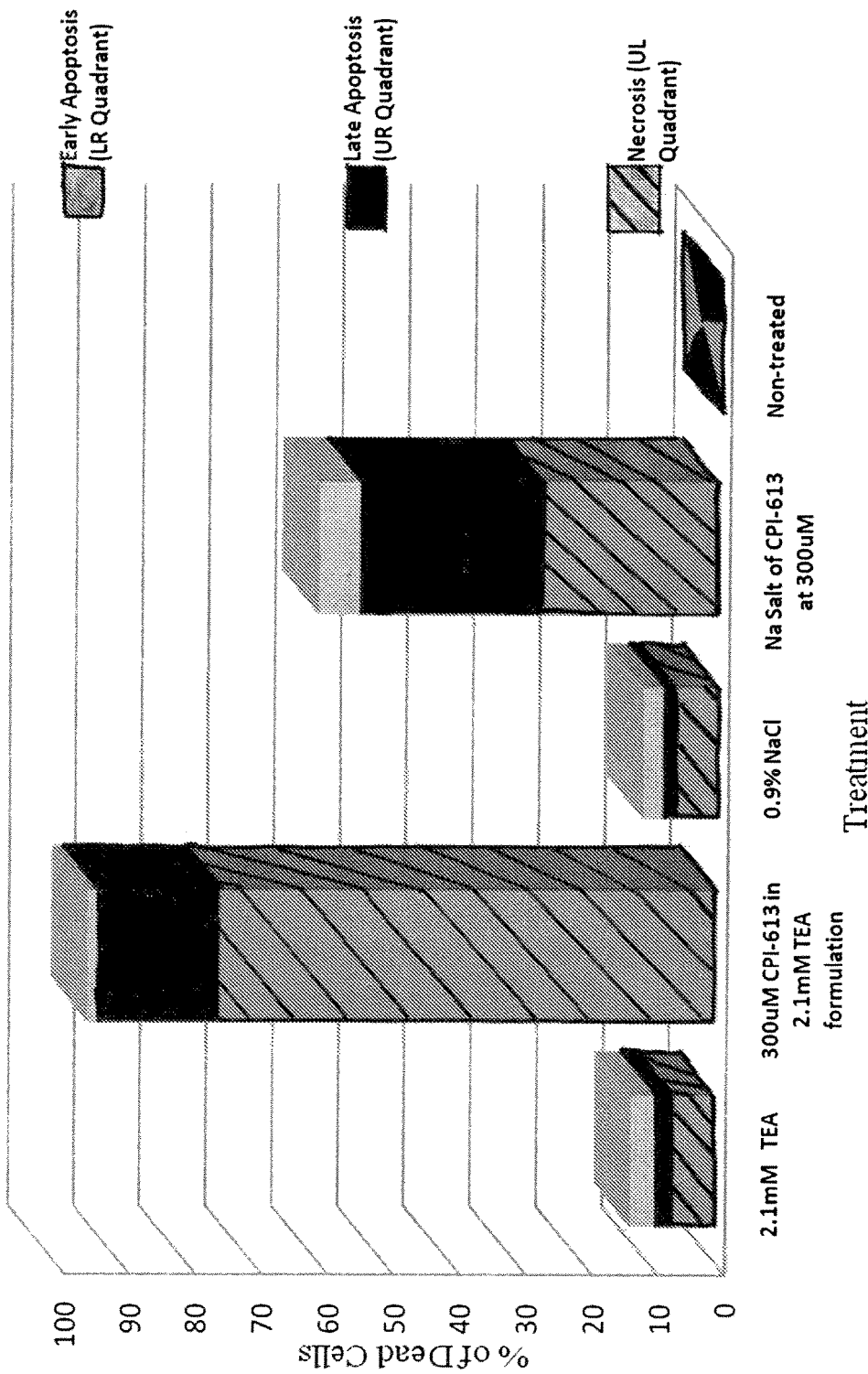
FIG. 15 is a bar graph showing the percentage of dead cells and the mechanism of cell death (i.e., apoptosis or necrosis) following administration of CPI-613 in triethanolamine or CPI-613 sodium salt.
Figure 16:
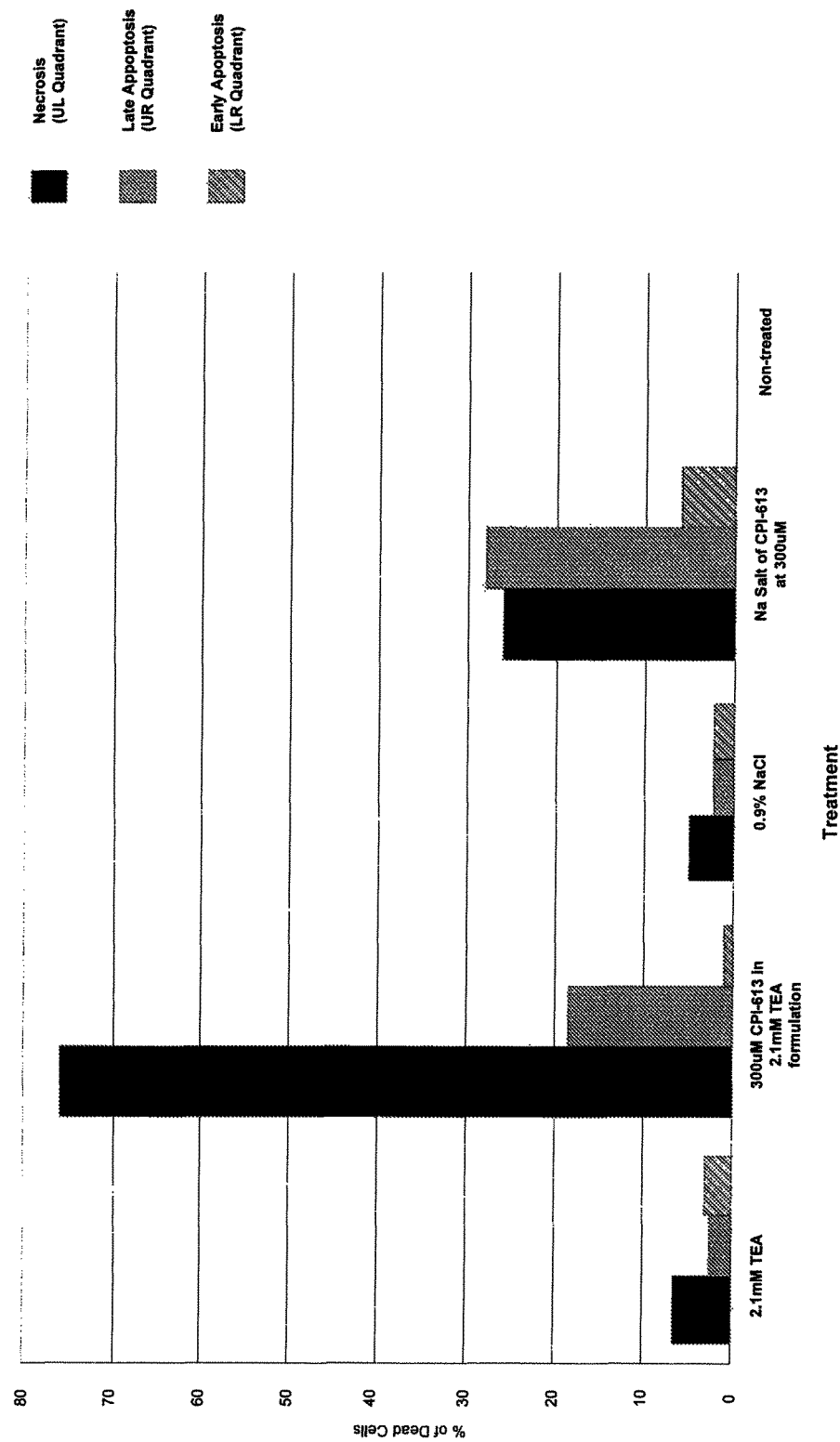
FIG. 16 is a bar graph showing the percentage of dead cells and the mechanism of cell death (i.e., apoptosis or necrosis) following administration of CPI-613 in triethanolamine or CPI-613 sodium salt.
Figure 17:
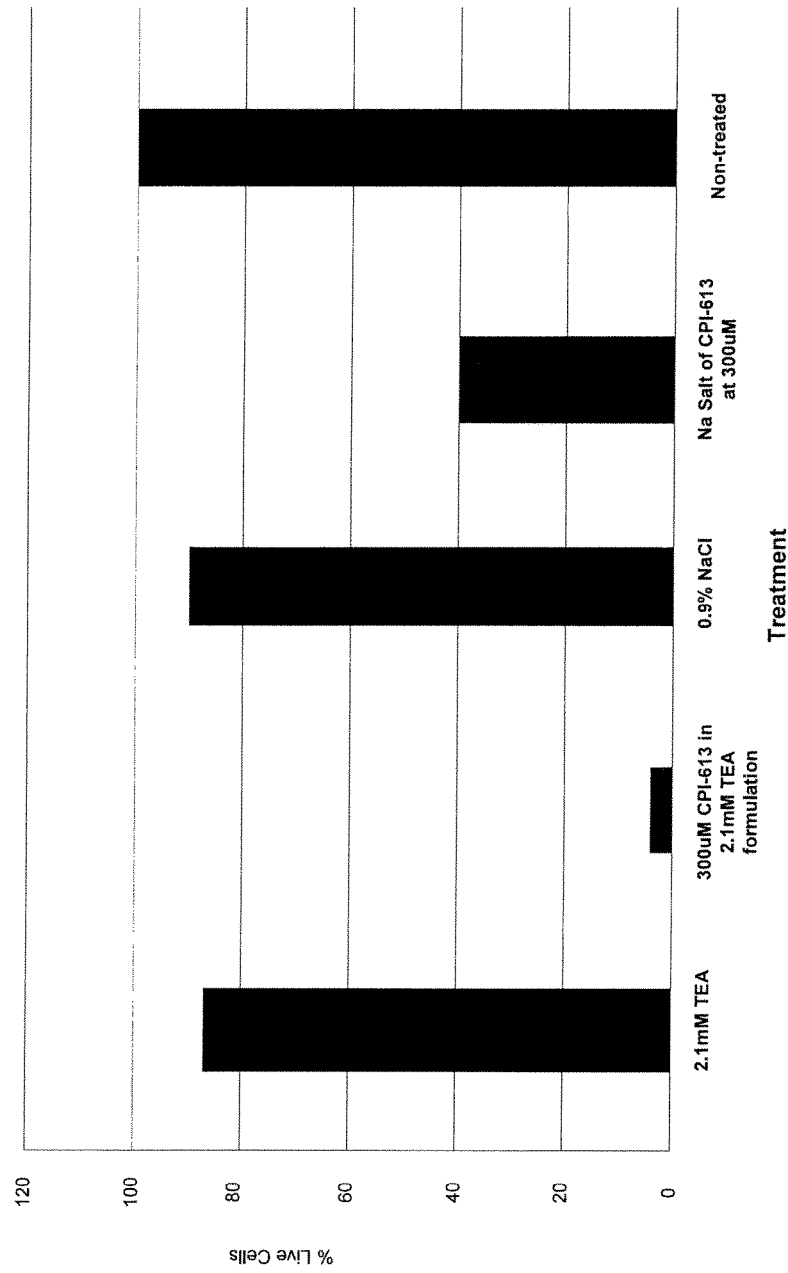
FIG. 17 is a bar graph showing the percentage of live cells following administration of CPI-613 in triethanolamine or CPI-613 sodium salt.

Results:

Data from the experiment is shown in FIGS. 15-17. The data seems to indicate a difference between the type of cell death (early apoptosis, late apoptosis, or necrosis) observed when comparing the TEA formulation of CPI-613 to the sodium salt formulation of CPI-613. The results from the TEA formulation indicate an increase in the number of cells in the state of necrotic death versus the number of cells in the state of apoptotic death. In contrast, the sodium salt formulation of CPI-613 showed a higher number of cells in the state of apoptotic death versus the number of cells in the state of necrotic death.

INCORPORATION BY REFERENCE

The entire disclosure of each of the patent documents and scientific articles referred to herein is incorporated by reference for all purposes.

EQUIVALENTS

The invention may be embodied in other specific forms without departing from the spirit or essential characteristics thereof. The foregoing embodiments are therefore to be considered in all respects illustrative rather than limiting the invention described herein. The scope of the invention is thus indicated by the appended claims rather than by the foregoing description, and all changes that come within the meaning and range of equivalency of the claims are intended to be embraced therein.

What is claimed is:

1. A method of treating a cancer selected from the group consisting of carcinoma, sarcoma, myeloma, lymphoma, leukemia and cancer of the pancreas, comprising the step of intravenously administering to a human patient in need thereof a pharmaceutical formulation comprising:
   a) therapeutically effective amount of a compound of Formula I:

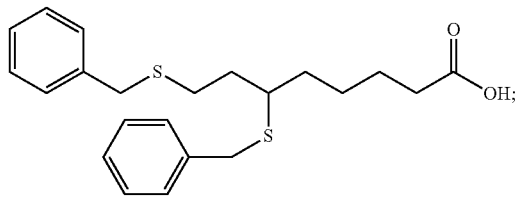

(Formula I)

and
   b) at least one ion pairing agent.

2. The method of claim 1, wherein the at least one ion pairing agent comprises a tertiary amine.

3. The method of claim 1, wherein the at least one ion pairing agent comprises triethanolamine, polyethyleneimine, diethanolamine, monoethanolamine, mefenamic acid, tromethamine, or a combination thereof.

4. The method of claim 1, wherein the at least one ion pairing agent comprises triethanolamine.

5. The method of claim 1, wherein the at least one ion pairing agent and the compound of Formula I are present in a molar ratio of 20:1 to 1:20.

6. The method of claim 1, wherein the cancer is a carcinoma, sarcoma, myeloma, lymphoma, or leukemia.

7. The method of claim 6, wherein the cancer is a lymphoma.

8. The method of claim 6, wherein the cancer is a leukemia.

9. The method of claim 6, wherein the cancer is a carcinoma.

10. The method of claim 6, wherein the cancer is a sarcoma.

11. The method of claim 6, wherein the cancer is a myeloma.

12. The method of claim 1, wherein the cancer is a cancer of the pancreas.

13. The method of claim 1, wherein the compound of Formula I is administered at a dose of 0.001 mg/m$^2$ to 10 g/m$^2$.

14. The method of claim 13, wherein the compound of Formula I is administered at a dose of 0.01 mg/m$^2$ to 5 g/m$^2$.

15. The method of claim 14, wherein the compound of Formula I is administered at a dose of 0.25 mg/m$^2$ to 3 g/m$^2$.

16. The method of claim 7, wherein the compound of Formula I is administered at a dose of 0.25 mg/m to 3 g/m$^2$.

17. The method of claim 8, wherein the compound of Formula I is administered at a dose of 0.25 mg/m$^2$ to 3 g/m$^2$.

18. The method of claim 12, wherein the compound of Formula I is administered at a dose of 0.25 mg/m$^2$ to 3 g/m$^2$.

19. A method of treating a cancer selected from the group consisting of carcinoma, sarcoma, myeloma, lymphoma, leukemia and cancer of the pancreas, comprising the step of intravenously administering to a human patient in need thereof a pharmaceutical formulation comprising:
   a) a therapeutically effective amount of a compound of Formula I:

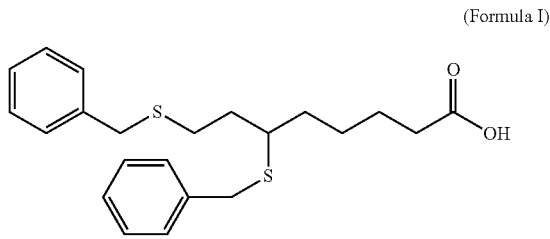 [SMILES: O=C(O)CCCCC(CCSCc1ccccc1)SCc1ccccc1]

(Formula I)

or a salt thereof; and
   b) at least one ion pairing agent.

20. The method of claim 19, wherein the cancer is a lymphoma and the compound of Formula I or salt thereof is administered at a dose of 0.25 mg/m$^2$ to 3 g/m$^2$.

21. The method of claim 19, wherein the cancer is a leukemia and the compound of Formula I or salt thereof is administered at a dose of 0.25 mg/m$^2$ to 3 g/m$^2$.

22. The method of claim 19, wherein the cancer is a cancer of the pancreas and the compound of Formula I or salt thereof is administered at a dose of 0.25 mg/m² to 3 g/m².

* * * * *